United States Patent
McGee et al.

(10) Patent No.: US 10,101,335 B2
(45) Date of Patent: Oct. 16, 2018

(54) METHODS FOR MASS SPECTROMETRIC BASED CHARACTERIZATION OF BIOLOGICAL MOLECULES

(71) Applicant: Thermo Finnigan LLC, San Jose, CA (US)

(72) Inventors: William M. McGee, Watertown, MA (US); Helene L. Cardasis, Mountain View, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 15/406,601

(22) Filed: Jan. 13, 2017

(65) Prior Publication Data
US 2017/0205424 A1  Jul. 20, 2017

Related U.S. Application Data

(60) Provisional application No. 62/278,942, filed on Jan. 14, 2016.

(51) Int. Cl.
*G01N 33/68* (2006.01)
*H01J 49/00* (2006.01)
(Continued)

(52) U.S. Cl.
CPC ...... *G01N 33/6848* (2013.01); *H01J 49/0031* (2013.01); *H01J 49/0072* (2013.01); *H01J 49/165* (2013.01)

(58) Field of Classification Search
USPC ....... 250/281–283, 285, 288, 289, 290, 293, 250/298, 299, 526; 436/86, 171, 174,
(Continued)

(56) References Cited

U.S. PATENT DOCUMENTS 5,175,430 A   12/1992  Enke et al.
7,064,317 B2   6/2006  McLuckey et al.
(Continued)

FOREIGN PATENT DOCUMENTS

GB    2476603 A       6/2011
WO    02/086490 A2   10/2002
(Continued)

OTHER PUBLICATIONS

Bern et al., "Identification of Peptides from Ion-Trap Data-Independent Tandem MS", Poster, Proceedings of the 56th ASMS Conference on Mass Spectrometry and Allied Topics, Denver, CO, Jun. 1-5, 2008.
(Continued)

*Primary Examiner* — Bernard Souw
(74) *Attorney, Agent, or Firm* — Thomas F. Cooney

(57) ABSTRACT

Applications of ion-ion reaction chemistry are disclosed in which proton transfer reactions (PTR) combined with higher-collision-energy dissociation (HCD) are used to (1) simplify complex mixture analysis of samples introduced into a mass spectrometer, and (2) improve resolution and sensitivity for the analysis of large proteins in excess of 50 kDa by removing charge, reducing the collisional cross section, and, in several cases, enhancing the sequence coverage obtained.

14 Claims, 24 Drawing Sheets

(51) Int. Cl.
*B01D 59/44* (2006.01)
*H01J 49/16* (2006.01)

(58) Field of Classification Search
USPC .................. 436/183; 435/23, 24; 702/27, 76
See application file for complete search history.

(56) References Cited

U.S. PATENT DOCUMENTS

| | | | |
|---|---|---|---|
| 7,297,941 B2 | 11/2007 | Senko et al. | |
| 7,355,169 B2 | 4/2008 | McLuckey et al. | |
| 7,511,267 B2 | 3/2009 | Zabrouskov | |
| 7,518,108 B2 | 4/2009 | Frey et al. | |
| 7,550,718 B2 | 6/2009 | McLuckey et al. | |
| 7,749,769 B2 * | 7/2010 | Hunt .................. | G01N 33/6818 250/290 |
| 8,053,723 B2 | 11/2011 | Senko | |
| 8,148,677 B2 | 4/2012 | Zhang et al. | |
| 8,168,943 B2 | 5/2012 | Schwartz et al. | |
| 8,283,626 B2 | 10/2012 | Brown et al. | |
| 8,334,503 B2 | 12/2012 | McLuckey et al. | |
| 8,440,962 B2 | 5/2013 | Le Blanc | |
| 8,809,770 B2 | 8/2014 | Bonner et al. | |
| 8,809,772 B2 | 8/2014 | Bonner et al. | |
| 8,935,101 B2 | 1/2015 | Wright | |
| 9,269,553 B2 | 2/2016 | Bonner et al. | |
| 9,837,255 B2 * | 12/2017 | Stephenson, Jr. ... | H01J 49/0072 |
| 2002/0172961 A1 * | 11/2002 | Schneider ............ | C12Q 1/6872 435/6.12 |
| 2004/0069943 A1 | 4/2004 | Kato | |
| 2005/0098719 A1 | 5/2005 | Thomson | |
| 2008/0093546 A1 | 4/2008 | Hartmer | |
| 2008/0093547 A1 | 4/2008 | Hartmer et al. | |
| 2008/0128607 A1 | 6/2008 | Herold et al. | |
| 2011/0114835 A1 | 5/2011 | Chen et al. | |
| 2011/0189788 A1 | 8/2011 | Brown et al. | |
| 2012/0156707 A1 | 6/2012 | Hartmer et al. | |
| 2012/0205531 A1 | 8/2012 | Zabrouskov | |
| 2013/0084645 A1 * | 4/2013 | Coon .................. | G01N 33/483 436/173 |
| 2014/0120565 A1 | 5/2014 | Coon et al. | |
| 2014/0357502 A1 | 12/2014 | Campbell et al. | |
| 2015/0293058 A1 | 10/2015 | Wuhr et al. | |
| 2015/0380231 A1 * | 12/2015 | Brown .................. | H01J 49/428 250/282 |
| 2017/0162372 A1 * | 6/2017 | Stephenson, Jr. ... | H01J 49/0072 |
| 2017/0205424 A1 * | 7/2017 | McGee .............. | G01N 33/6848 |
| 2017/0205425 A1 * | 7/2017 | Yip .................... | G01N 33/6848 |
| 2017/0205426 A1 * | 7/2017 | Stephenson, Jr. ........ | C12Q 1/18 |

FOREIGN PATENT DOCUMENTS

| | | |
|---|---|---|
| WO | 2013/098603 A1 | 7/2013 |
| WO | 2013/166169 A1 | 11/2013 |
| WO | 2014/150040 A2 | 9/2014 |
| WO | 2016/011355 A1 | 1/2016 |

OTHER PUBLICATIONS

Campbell et al., "Targeted Ion Parking for the Quantitation of Biotherapeutic Proteins: Concepts and Preliminary Data", J Am Soc Mass Spectrom 2010, 21, pp. 2011-2022.
Cargile et al., "Identification of Bacteriophage MS2 Coat Proteinfrom *E. coli* Lysates via Ion Trap Collisional Activation of Intact Protein Ions", Anal. Chem. 2001, 73, pp. 1277-1285.
Chrisman et al., "Parallel Ion Parking of Protein Mixtures", Anal. Chem. 2006, 78, pp. 310-316.
Chrisman et al., "Parallel Ion Parking: Improving Conversion of Parents to First-Generation Products in Electron Transfer Dissociation", Anal. Chem. 2005, 77 (10), pp. 3411-3414.
Egertson et al., "Multiplexed MS /MS for improved data independentacquisition", Nature Methods, 2013, vol. 10 (8), pp. 744-748.
Gillet, et al., "Targeted Data Extraction of the MS/MS Spectra Generated by Data-independent Acquisition: A New Concept for Consistent and Accurate Proteome Analysis", Molecular & Cellular Proteomics 11.6, 2012, pp. 1-17.
He et al., "Dissociation of Multiple Protein Ion Charge States Following a Single Gas-Phase Purification and Concentration Procedure", Anal. Chem. 2002, pp. 4653-4661.
Liu et al., "Top-Down Protein Identification/Characterization of a Priori Unknown Proteins via Ion Trap Collision-Induced Dissociation and Ion/Ion Reactions in a Quadrupole/Time-of-Flight Tandem Mass Spectrometer", Anal. Chem. 2009, 81, pp. 1433-1441.
McLuckey et al., "Electrospray/Ion Trap Mass Spectrometry for the Detection and Identification of Organisms", joint services workshop on biological mass spectrometry, Baltimore, MD (United States), Jul. 28-30, 1997, https://www.osti.gov/scitech/biblio/622805, pp. 1-8.
McLuckey et al., "Ion Parking during Ion/Ion Reactions in Electrodynamic Ion Traps", Anal. Chem. 2002, 74, pp. 336-346.
McLuckey et al., "Ion/Ion Chemistry of High-Mass Multiply Charged Ions", Mass Spectrometry Reviews, 1998, 17, pp. 369-407.
McLuckey et al., "Ion/Ion Proton-Transfer Kinetics: Implications forAnalysis of Ions Derived from Electrospray of Protein Mixtures", Anal. Chem. 1998, 70, pp. 1198-1202.
McLuckey et al., "Ion/Molecule Reactions for Improved Effective Mass Resolution in Electrospray Mass Spectrometry", Anal. Chem. 1995, 67, pp. 2493-2497.
Panchaud et al., "Precursor Acquisition Independent From Ion Count: How to Dive Deeper into the Proteomics Ocean", Anal. Chem. 2009, 81, pp. 6481-6488.
Reid et al., "Gas-Phase Concentration, Purification, and Identification ofWhole Proteins from Complex Mixtures", J. Am. Chem. Soc. 2002, 124, pp. 7353-7362.
Scalf et al., "Charge Reduction Electrospray Mass Spectrometry", Anal. Chem. 2000, 72, pp. 52-60.
Stephenson et al., "Charge Manipulation for Improved Mass Determination of High-mass Species and Mixture Components by Electrospray Mass Spectrometry", J. Mass Spectrom. 1998, 33, pp. 664-672.
Stephenson et al., "Ion-ion Proton Transfer Reactions of Bio-ions Involving Noncovalent Interactions: Holomyoglobin", J Am Soc Mass Spectrom 1997, 8, pp. 637-644.
Stephenson et al., "Ion/Ion Proton Transfer Reactions for ProteinMixture Analysis", Anal. Chem. 1996, 68, pp. 4026-4032.
Stephenson et al., "Ion/Ion Reactions for Oligopeptide Mixture Analysis: Application to Mixtures Comprised of 0.5-100 kDa Components", J Am Soc Mass Spectrom 1998, 9, pp. 585-596.
Stephenson et al., "Ion/Ion Reactions in the Gas Phase: Proton Transfer Reactions Involving Multiply-Charged Proteins", J. Am. Chem. Soc. 1996, 118, pp. 7390-7397.
Stephenson et al., "Simplification of Product Ion Spectra Derived from Multiply Charged Parent Ions via Ion/Ion Chemistry", Anal. Chem. 1998, 70, pp. 3533-3544.
Sutton et al., "Top-Down Analysis of the Low Molecular Weight Human Plasma Proteome Using Hybrid Ion Trap-Fourier Transform Mass Spectrometry", http://tools.thermofisher.com/content/sfs/brochures/AN-344-LC-MS-Human-Plasma-Proteome-AN62498-EN.pdf, 2016, pp. 1-6.
Venable et al., "Automated approach for quantitative analysis ofcomplex peptide mixtures from tandem mass spectra", Nature Methods, 2004, vol. 1 (1), pp. 1-7.
Xia et al., "Mutual Storage Mode Ion/Ion Reactions in a Hybrid Linear Ion Trap", J Am Soc Mass Spectrom 2005, 16, pp. 71-81.
Coon et al., "Protein identification using sequential ionionreactions and tandem mass spectrometry", PNAS 2005, vol. 102 (27), 9463-9468.
Horn, et al., "Automated Reduction and Interpretation of High Resolution Electrospray Mass Spectra of Large Molecules," J. Am. Soc. Mass Spectrom., vol. 11, No. 4., (2000), pp. 320-332.

* cited by examiner

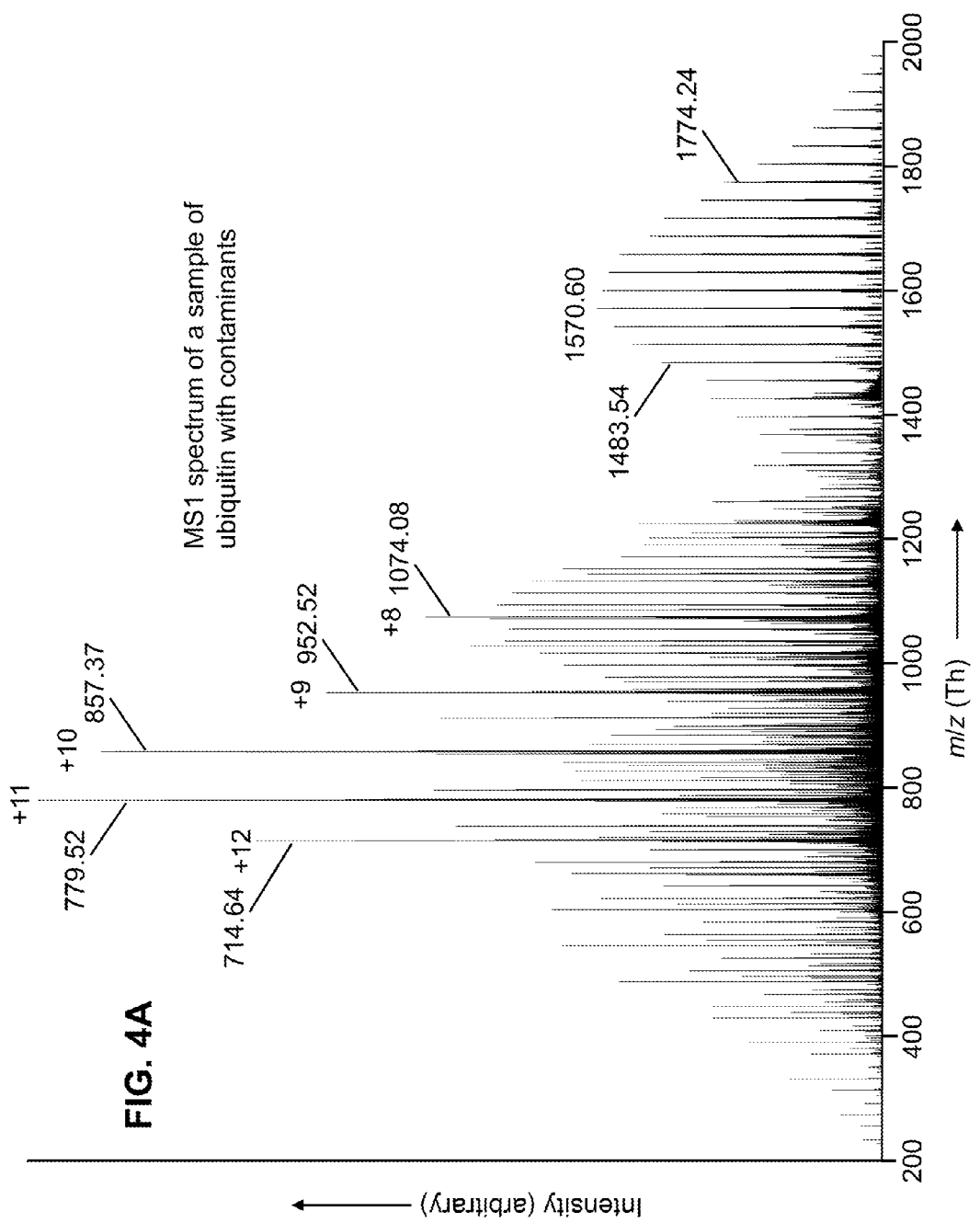

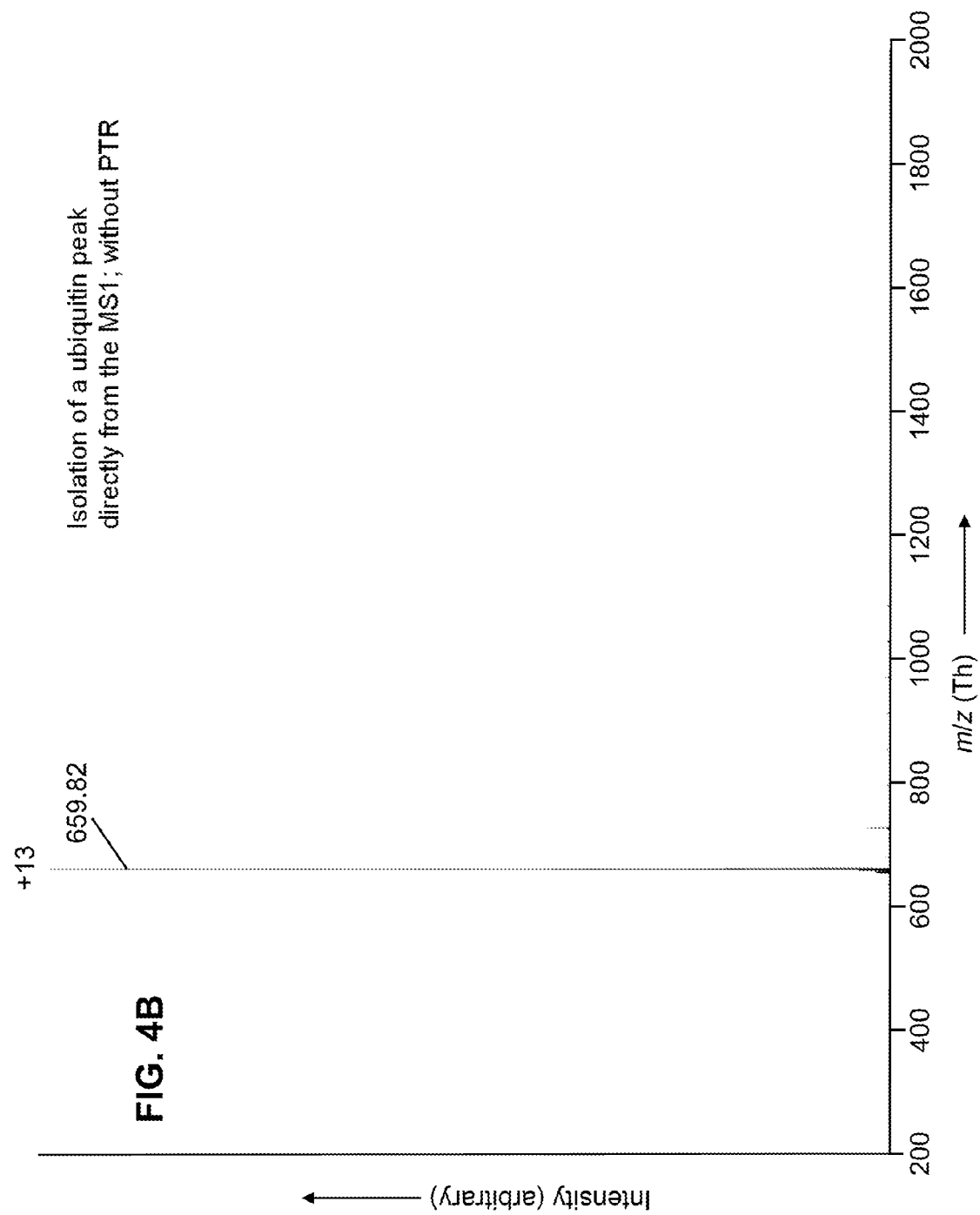

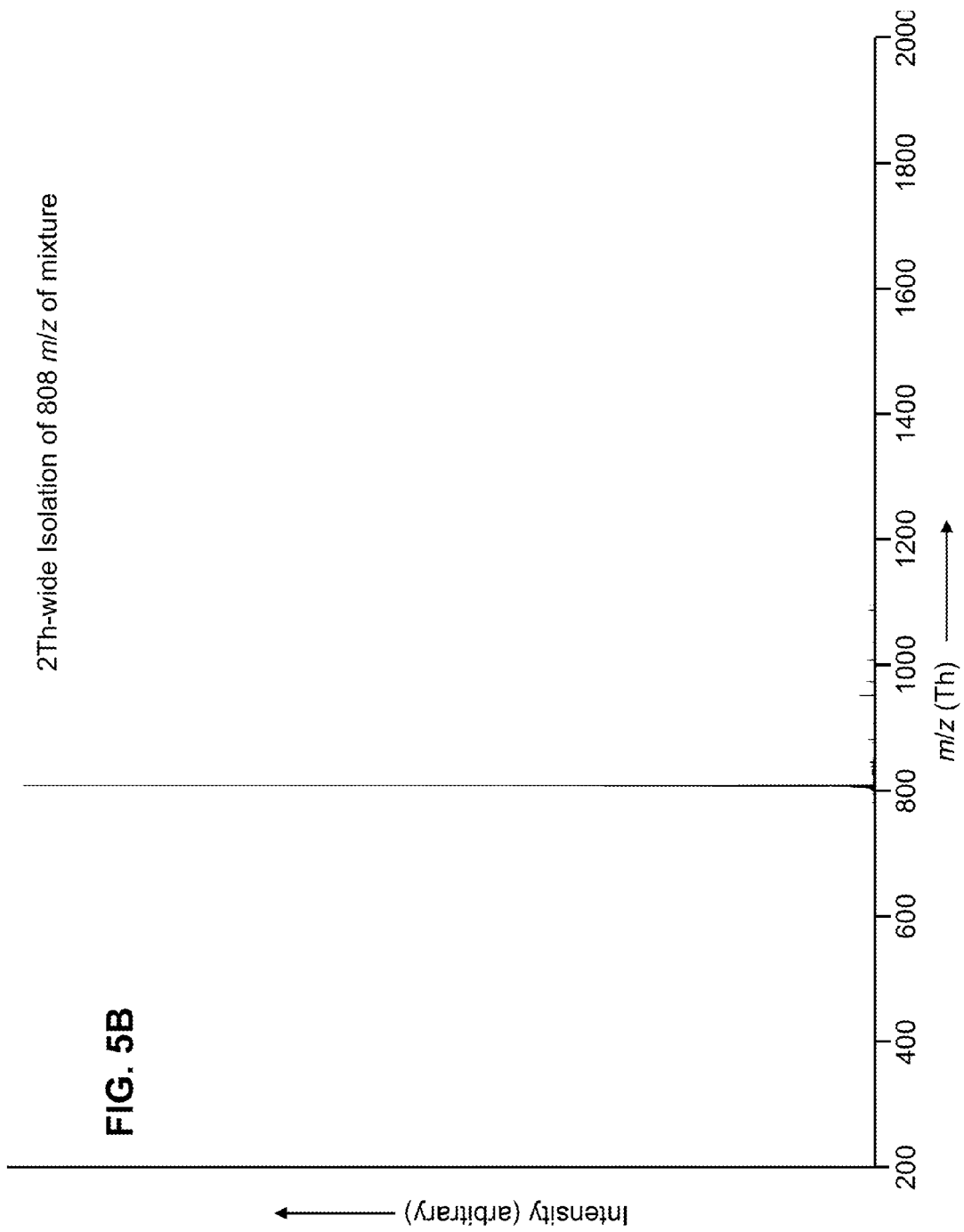

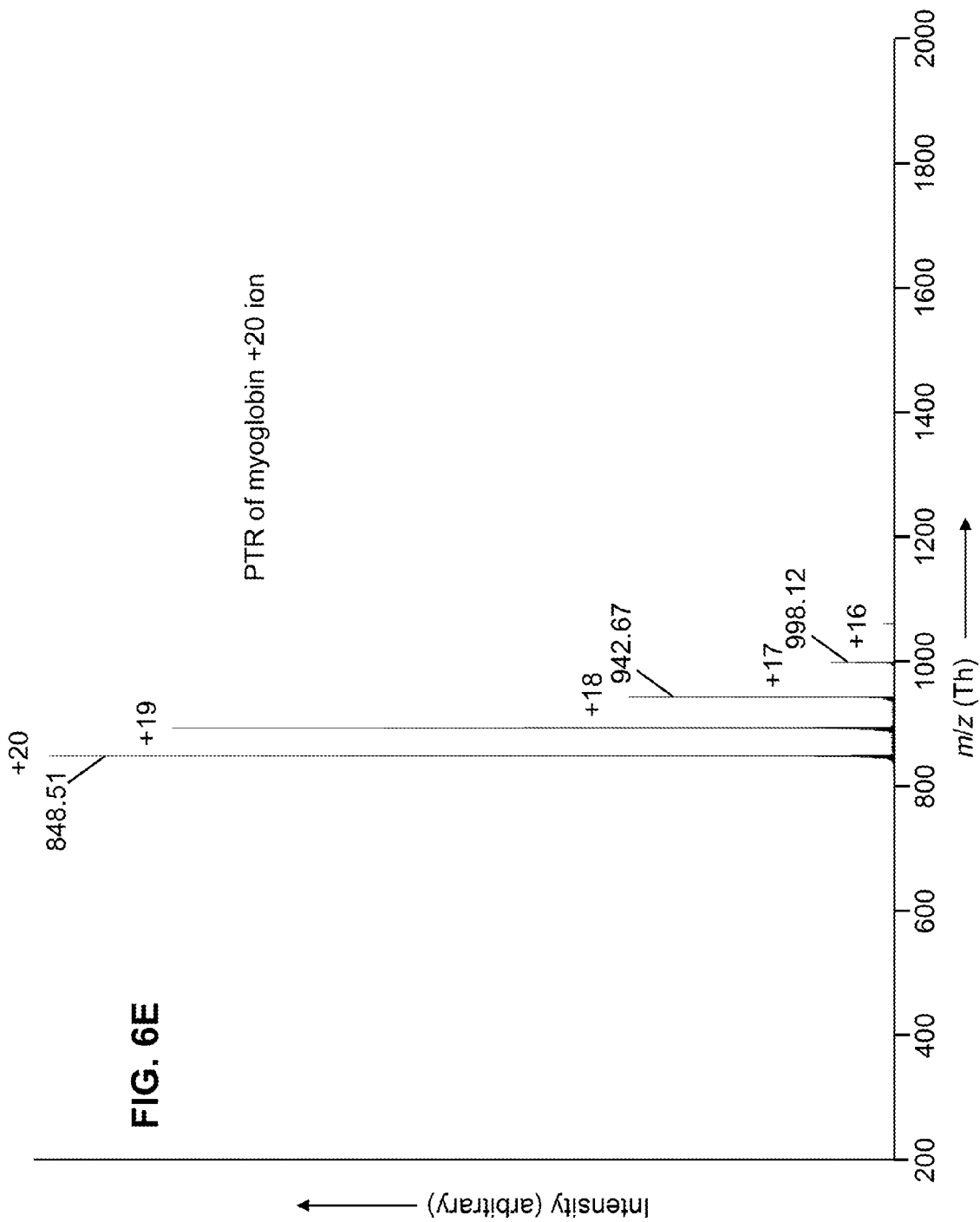

HCD of the spread charge state distribution

METHODS FOR MASS SPECTROMETRIC BASED CHARACTERIZATION OF BIOLOGICAL MOLECULES

CROSS REFERENCE TO RELATED APPLICATIONS

This application claims, under 35 U.S.C. § 119(e), priority to and the benefit of the filing date of commonly-assigned, U.S. Provisional Application No. 62/278,942, filed on Jan. 14, 2016 and titled "Methods for Mass Spectrometric Based Characterization of Biological Molecules", the disclosure of which is hereby incorporated by reference in its entirety. The subject matter of this application is also related to commonly-assigned and co-pending International Application No. PCT/US2015/040914, filed on Jul. 17, 2015 and titled "Methods for Mass Spectrometry of Mixtures of Proteins of Polypeptides Using Proton Transfer Reaction", the disclosure of which is hereby incorporated by reference in its entirety.

TECHNICAL FIELD

The present invention relates to mass spectrometry and, more particularly, relates to methods for purifying and analyzing complex mixtures of proteins or polypeptides by mass spectrometry of proton transfer reaction product ions generated from proteins, polypeptides, and other biologically relevant multiply-charged species and also to the application of these methods for obtaining sequenced based information necessary for identification and quantitation of biological species.

BACKGROUND ART

Over the last two decades, mass spectrometry has made tremendous strides in analyzing protein samples derived from a variety of different sample types. Coupled with electrospray ionization and various separation techniques, thousands of proteins may be identified and quantitated in a single sample. The most common approach used in the laboratory today involves some form of protein extraction followed by proteolytic digestion of protein sample of interest. The use of proteolytic enzymes like trypsin produces peptides that can easily be analyzed by a variety of different instrument configurations. This approach termed "bottom-up" proteomics, can be used to study the state of living cells as a function of their environment. One of the major advantages of the "bottom-up" approach is that the peptides produced have very similar physiochemical properties which makes for a straight forward separation of thousands of peptides in complex samples. Any separation approach coupled with tandem mass spectrometry can then be used to produce amino acid sequence information that is utilized to identify the proteins in a given sample. Although this technique is routine in many laboratories, there are limitations as to the amount of information that can be obtained when reducing intact proteins to their constituent peptides.

In contrast to "bottom-up" proteomics, "top-down" proteomics refers to methods of analysis in which protein samples are introduced intact into a mass spectrometer, without enzymatic, chemical or other means of digestion. Top-down analysis enables the study of the intact protein, allowing identification, primary structure determination and localization of post-translational modifications (PTMs) directly at the protein level. Top-down proteomic analysis typically consists of introducing an intact protein into the ionization source of a mass spectrometer, fragmenting the protein ions and measuring the mass-to-charge ratios and abundances of the various fragments so-generated. The resulting fragmentation is many times more complex than a peptide fragmentation, which may, in the absence of the methods taught herein, necessitate the use of a mass spectrometer with very high mass accuracy and resolution capability in order to interpret the fragmentation pattern with acceptable certainty. The interpretation generally includes comparing the observed fragmentation pattern to either a protein sequence database that includes compiled experimental fragmentation results generated from known samples or, alternatively, to theoretically predicted fragmentation patterns. For example, Liu et al. ("Top-Down Protein Identification/Characterization of a Priori Unknown Proteins via Ion Trap Collision-Induced Dissociation and Ion/Ion Reactions in a Quadrupole/Time-of-Flight Tandem Mass Spectrometer", *Anal. Chem.* 2009, 81, 1433-1441) have described top-down protein identification and characterization of both modified and unmodified unknown proteins with masses up to ≈28 kDa An advantage of a top-down analysis over a bottom-up analysis is that a protein may be identified directly, rather than inferred as is the case with peptides in a bottom-up analysis. Another advantage is that alternative forms of a protein, e.g. post-translational modifications and splice variants, may be identified. However, top-down analysis has a disadvantage when compared to a bottom-up analysis in that many proteins can be difficult to isolate and purify. Thus, each protein in an incompletely separated mixture can yield, upon mass spectrometric analysis, multiple ion species, each species corresponding to a different respective degree of protonation and a different respective charge state, and each such ion species can give rise to multiple isotopic variants.

The process of analyzing intact proteins in cell lysates by mass spectrometry (MS) is associated with a number of difficulties. Firstly, electrospray ionization (ESI) of protein mixtures from cell lysates can generate extremely complex mass spectra due to the presence of multiple proteins, each comprising its own charge state envelope, where each charge state envelope is the collection of mass spectral lines corresponding to plural charge states, and where each charge state correlates directly with the number of positively charged protons that are adducted to an otherwise charge-free molecule. Consequently, multiple charge state envelopes may be overlapping within any given mass-to-charge (m/z) range. In this example, multiple proteins overlap at the same m/z value that have different molecular weights and charges. Commonly used techniques in MS are often insufficient for simplifying these spectra because of the inherent peak overlapping as well as the inherent wide range of magnitudes of MS lines of ionized constituents, where such constituents may range from uninteresting small molecules to interfering biomolecules to the proteins of interest, themselves. Isolation of a specified charge state of a protein within such complex spectra does not typically alleviate the burden of multiple protein peaks overlapping, since the isolation of ions of a particular protein charge state will generally result in co-isolation of one or more additional ions. This co-isolation makes it a challenge not only to dissociate the protein in an attempt to identify it based on the fragments produced, but also to accurately determine the intact mass and sequence coverage of that protein.

So-called "front-end" separation techniques, such as liquid chromatography (LC) or ion mobility spectrometry (IMS), performed prior to introduction of samples into a mass spectrometer, may be implemented to reduce the overall complexity and provide an additional major benefit, which is the reduction of ionization competition at an ionization source. Unlike mixtures of proteolytic peptides typically analyzed in bottom-up experiments, intact proteins mixtures contain a wide range of molecular weights, isoelectric points, hydrophobicities, and other physiochemical properties that make it challenging to analyze these mixtures via any single separation technique in a comprehensive manner. Both of the above separation methods are associated with their own benefits and pitfalls. Liquid chromatography tends to require significant amounts of time per sample to separate individual proteins, although it is still common to have two or more proteins co-elute. Enhanced separation can reach the point of becoming more of "an art" than a standardized method, and the enhanced separation may be dependent on the user skill in the state-of-the-art. The latter technique, IMS, can rapidly separate certain proteins and/or charge states from others but IMS spectra are at least partially correlative with (i.e., not "orthogonal to") mass spectra. The IMS method also suffers from ionization competition, requires extensive optimization and typically involves dynamic conditions to observe a full mass spectrum containing all charge states.

Proton transfer reactions, a type of ion-ion reaction that has been used extensively in biological applications for rapid separations of complex mixtures, addresses many of these aforementioned concerns. Experimentally, proton transfer is accomplished by causing multiply-positively-charged protein ions from a sample to react with introduced singly-charged reagent anions so as to reduce the charge of the multiply-charged protein ions. These reactions proceed with pseudo-first order reaction kinetics when the anions are present in large excess over the protein ion population. The rate of reaction is directly proportional to the square of charge of the protein ion (or other multiply-charged cation) multiplied by the charge on the anion. The same relationship holds for reactions of the opposite polarity as well. This produces a series of pseudo-first order consecutive reaction curves as defined by the starting multiply-charged protein ion population. Although the reactions are highly exothermic (in excess of 100 kcal/mol), proton transfer is an even-electron process performed in the presence of 1 mtorr of background gas (i.e. helium) and thus does not fragment the starting multiply-charged protein ion population. The collision gas serves to remove the excess energy on the microsecond time scale ($10^8$ collisions per second), thus preventing fragmentation of the resulting product ion population.

Proton transfer reactions (PTR) have been used successfully to identify individual proteins in mixtures of proteins. This mixture simplification process has been employed to determine charge state and molecular weights of high mass proteins. PTR has also been utilized for simplifying product ion spectra derived from the collisional-activation of multiply-charged precursor protein ions. Although PTR reduces the overall signal derived from multiply-charged protein ions, this is more than offset by the significant gain in signal-to-noise ratio of the resulting PTR product ions. The PTR process is 100% efficient leading to only single series of reaction products, and no side reaction products that require special interpretation and data analysis.

Various aspects of the application of PTR to the analysis of peptides, polypeptides and proteins have been described in the following documents: U.S. Pat. No. 7,749,769 B2 in the names of inventors Hunt et al., U.S. Patent Pre-Grant Publication No. 2012/0156707 A1 in the names of inventors Hartmer et al., U.S. Pre-Grant Publication No. 2012/0205531 A1 in the name of inventor Zabrouskov; McLuckey et al., *Anal. Chem.* 1998, 70:1198-1202; Stephenson et al., *J. Am. Soc. Mass Spectrom.* 1998, 8:637-644; Stephenson et al., *J. Am. Chem. Soc.* 1996, 118:7390-7397; McLuckey et al., *Anal. Chem.* 1995, 67:2493-2497; Stephenson et al., *Anal. Chem.* 1996, 68:4026-4032; Stephenson et al., *J. Am. Soc. Mass Spectrom.* 1998, 9:585-596; Stephenson et al., *J. Mass Spectrom.* 1998, 33:664-672; Stephenson et al., *Anal. Chem.*, 1998, 70:3533-3544 and Scalf et al., *Anal. Chem.* 2000, 72:52-60. Various aspects of general ion/ion chemistry have been described in McLuckey and Stephenson, *Mass Spec Reviews* 1998, 17:369-407 and U.S. Pat. No. 7,550,718 B2 in the names of inventors McLuckey et al. Apparatus for performing PTR and for reducing ion charge states in mass spectrometers have been described in U.S. Pre-Grant Publication No. 2011/0114835 A1 in the names of inventors Chen et al., U.S. Pre-Grant Publication No. 2011/0189788 A1 in the names of inventors Brown et al., U.S. Pat. No. 8,283,626 B2 in the names of inventors Brown et al. and U.S. Pat. No. 7,518,108 B2 in the names of inventors Frey et al. Adaptation of PTR charge reduction techniques to detection and identification of organisms has been described by McLuckey et al. ("*Electrospray/Ion Trap Mass Spectrometry for the Detection and Identification of Organisms*", Proc. First Joint Services Workshop on Biological Mass Spectrometry, Baltimore, Md., 28-30 Jul. 1997, 127-132).

The product ions produced by the PTR process can be accumulated into one or into several charge states by the use of a technique known as "ion parking". Ion parking uses supplementary AC voltages to consolidate the PTR product ions formed from the original variously protonated ions of any given protein molecule into a particular charge state or states at particular m/z values during the reaction period. This technique can be used to concentrate the product ion signal into a single or limited number of charge states (and, consequently, into a single or a few respective mass-to-charge [m/z] values) for higher sensitivity detection or further manipulation using collisional-activation, ETD, or other ion manipulation techniques. Various aspects of ion parking have been described in U.S. Pat. No. 8,440,962 B2 in the name of inventor Le Blanc and in the following documents: McLuckey et al., *Anal. Chem.* 2002, 74:336-346; Reid et al., *J. Am. Chem. Soc.* 2002, 124:7353-7362; He et al., *Anal. Chem.* 2002, 74:4653-4661; Xia et al., *J. Am. Soc. Mass. Spectrom.* 2005, 16:71-81; Chrisman et al., *Anal. Soc. Mass. Spectrom.* 2005, 77:3411-3414 and Chrisman et al., *Anal. Chem.* 2006, 78:310-316.

Another difficulty associated with the mass spectrometric analysis of proteins in cell lysates by (MS) is that the fragmentation behavior for each charge state of a protein is generally unknown prior to the dissociation event. In particular, ions comprising some charge states can dissociate well while ions comprising other charge states may dissociate poorly. Isolation and dissociation of ions of a particular charge state therefore does not guarantee efficient dissociation or dissociation into a set of diagnostic fragments.

A third challenge associated with intact protein analysis is the wide distribution of charge states produced for high molecular weight proteins typically in excess of 50 kDa. Here the starting signal can be divided into over 30 plus charge states, making tandem mass spectrometry of any given charge state produce a spectrum with low signal-to-noise ratio. The ability to produce ample sequence coverage for protein identification can therefore be difficult with a single tandem mass spectrum.

A variety of ion activation (fragmentation) techniques can be used to produce structural information on intact proteins. The most commonly used approach termed collision-induced dissociation (CID) involves collisions of an isolated population of multiply-charged precursor ions with a neutral background gas. Most commonly, the multiply-charged precursor ions are accelerated using the fundamental frequency of motion of the defined ion population in order to collide with the neutral background gas so as to produce unimolecular dissociation events. This process leads to fragmentation along the amide backbone of the protein thus yielding amino acid sequence information. More extensive fragmentation of proteins can be obtained with higher collision energy processes termed HCD or high energy collision induced dissociation. Many times this involves multiple fragmentation events inside the collision cell thus producing more extensive sequence coverage. Another approach used to produce protein sequence coverage via ion activation is that of photodissociation (PD), where photons of a defined wavelength are used to excite the ion of interest. Two common types employed include ultra-violet (UV-PD) and infrared multiphoton dissociation (IRMPD). The latter is a high energy process where the rate of energy deposition in the ion far exceeds that of the dissociation process. Here fragmentation can be produced along any point in the protein backbone, or may yield amino acid side chain fragmentation as well. For IRMPD, this is a much lower energy process that is characterized by the presence of cleavages at amide bonds and losses of ammonia and water from the intact protein and fragment ions generated during irradiation. The time frame of the IRMPD experiment can be expanded to produce more extensive fragmentation as well. Ion-ion reactions using electron transfer reagent ions can also be employed as a fragmentation approach for intact proteins. Here an electron transfer event from the multiple-charged protein to the singly-charged anion produces backbone fragmentation of the protein with any posttranslational modifications still intact.

Taken together, these ion activation approaches for tandem mass spectrometry produce many different complementary forms of fragmentation that can provide protein sequence information. Ideally, these approaches can be applied in a broad band fashion in order to increase sequence coverage of proteins and provide additional information on modifications, splice variants, and expression of single amino acid mutations. The application of these approaches in a broadband format (i.e. covering multiple charge states of the same intact protein) would provide a more comprehensive view of protein characterization and identification.

SUMMARY OF THE INVENTION

The present disclosure teaches mass spectrometric methods that employ proton transfer reactions (PTR) in combination with ion parking techniques followed by higher-collisional energy dissociation (HCD) so at to yield broad m/z-band activation and fragmentation. The intended results provide simplified spectral analysis with enhanced spectral information. The present disclosure teaches the methods of targeted, data-dependent and data-independent mass spectral analysis using the PTR and HCD techniques in combination.

The methods disclosed herein incorporate benefits from both PTR and HCD in a synergistic manner. During an analysis of a complex mass spectrum generated from a natural sample, an isolation window may be selected and subjected to PTR, preferably in combination with the ion parking technique, such that the precursor ion or ions are charge reduced to a pre-set m/z range. Any co-isolated low-charge-state ions that may be present in the chosen isolation window will likely not fall into the new charge state m/z range. This procedure can filter proteins from contaminant or low-charged ions, effectively purifying the desired protein ions. Following the PTR and ion parking, a second PTR event may be implemented to redistribute the signal form a single purified protein charge state to multiple lesser (lower) charge states. The newly formed charge state envelope(s) of the protein(s) extracted from the initial isolation may then be subjected to HCD. The HCD collision energy may be chosen such that the higher charge states are dissociated while the lower charge states maintain at least a portion of the intact (i.e., un-fragmented) protein-ion m/z values, such that the intact mass of the molecular ion can be readily identified and such that over-fragmentation (further fragmentation of already-formed fragments) is prevented or significantly reduced.

Experimentally, proton transfer reactions may be performed by causing multiply-positively-charged protein ions (i.e., protein cations) from a sample to react with singly-charged reagent anions so as to reduce the charge state of an individual protein cation and the number of such charge states of the protein cations. These reactions proceed with pseudo-first order reaction kinetics when the reagent anions are present in large excess over the protein cation population. The rate of reaction is directly proportional to the square of charge of the protein cation (or other multiply-charged cation) multiplied by the charge on the reagent anion. Consequently, more highly-charged proteins will react at a faster rate than lower charge states. The result of these reactions is a reduction of the charge state, z, of various multi-protonated proteins, leading to an increase in the m/z ratios. This process can lead to a reduction in spectral complexity by expanding the m/z range of a previously isolated sub-population of protein ions into an extended m/z range. The m/z ratios of lower-charged small molecule contaminants increase less rapidly or not at all, leading to a separation and purification of the spectral signatures of protein molecules The PTR process is 100% efficient leading to only single series of reaction products, and no side reaction products that require special interpretation and data analysis. Although the PTR reactions are highly exothermic (in excess of 100 kcal/mol), proton transfer is an even-electron process performed in the presence of 1 mtorr of background gas (i.e. helium) and thus does not fragment the starting multiply-charged protein cation population. The collision gas serves to remove the excess energy on the microsecond time scale ($10^8$ collisions per second), thus preventing fragmentation of the resulting product ion population. This technique may be used in conjunction with either data-dependent or data-independent methods.

During mass spectral analysis of a complex spectrum in accordance with the present teachings, PTR may be implemented by subjecting ions from a specified m/z window to the charge reduction reaction followed by either further tandem mass spectrometry events or mass analyses. This sequence of events may be considered to be a portion of a data-dependent method, because of the targeted approach using a specified m/z window. Alternatively, a data-independent approach may be implemented by isolating ions within adjacent and consecutive m/z windows of set widths, subjecting the so-isolated ions to PTR and performing either tandem mass spectrometry events or mass analyses on the so-formed PTR reaction products.

The same relationships described above also hold for opposite-polarity PTR reactions, defined here as reactions between singly-charged reagent cations and a population of multiply-charged anions derived from a protein sample. Various aspects of the application of PTR to the analysis of peptides, polypeptides and proteins have been described in the following documents: U.S. Pat. No. 7,749,769 B2 in the names of inventors Hunt et al., U.S. Patent Pre-Grant Publication No. 2012/0156707 A1 in the names of inventors Hartmer et al., U.S. Pre-Grant Publication No. 2012/0205531 A1 in the name of inventor Zabrouskov; McLuckey et al., "Ion/Ion Proton-Transfer Kinetics: Implications for Analysis of Ions Derived from Electrospray of Protein Mixtures", *Anal. Chem.* 1998, 70, 1198-1202; Stephenson et al., "Ion-ion Proton Transfer Reactions of Bio-ions Involving Noncovalent Interactions: Holomyoglobin", *J. Am. Soc. Mass Spectrom.* 1998, 8, 637-644; Stephenson et al., "Ion/Ion Reactions in the Gas Phase: Proton Transfer Reactions Involving Multiply-Charged Proteins", *J. Am. Chem. Soc.* 1996, 118, 7390-7397; McLuckey et al., "Ion/Molecule Reactions for Improved Effective Mass Resolution in Electrospray Mass Spectrometry", *Anal. Chem.* 1995, 67, 2493-2497; Stephenson et al., "Ion/Ion Proton Transfer Reactions for Protein Mixture Analysis", *Anal. Chem.* 1996, 68, 4026-4032; Stephenson et al., "Ion/Ion Reactions for Oligopeptide Mixture Analysis: Application to Mixtures Comprised of 0.5-100 kDa Components", *J. Am. Soc. Mass Spectrom.* 1998, 9, 585-596; Stephenson et al., "Charge Manipulation for Improved Mass Determination of High-mass Species and Mixture Components by Electrospray Mass Spectrometry", *J. Mass Spectrom.* 1998, 33, 664-672; Stephenson et al., "Simplification of Product Ion Spectra Derived from Multiply Charged Parent Ions via Ion/Ion Chemistry", *Anal. Chem.*, 1998, 70, 3533-3544 and Scalf et al., "Charge Reduction Electrospray Mass Spectrometry", *Anal. Chem.* 2000, 72, 52-60. Various aspects of general ion/ion chemistry have been described in McLuckey et al., "Ion/Ion Chemistry of High-Mass Multiply Charged Ions", *Mass Spectrom. Rev.* 1998, 17, 369-407 and U.S. Pat. No. 7,550,718 B2 in the names of inventors McLuckey et al. Apparatus for performing PTR and for reducing ion charge states in mass spectrometers have been described in U.S. Pre-Grant Publication No. 2011/0114835 A1 in the names of inventors Chen et al., U.S. Pre-Grant Publication No. 2011/0189788 A1 in the names of inventors Brown et al., U.S. Pat. No. 8,283,626 B2 in the names of inventors Brown et al. and U.S. Pat. No. 7,518,108 B2 in the names of inventors Frey et al. Adaptation of PTR charge reduction techniques to detection and identification of organisms has been described by McLuckey et al. ("*Electrospray/Ion Trap Mass Spectrometry for the Detection and Identification of Organisms*", Proc. First Joint Services Workshop on Biological Mass Spectrometry, Baltimore, Md., 28-30 Jul. 1997, 127-132).

Proton transfer reactions proceed rapidly as a result of their thermodynamic favorability. Neutralization and charge reduction reactions such as PTR are almost exclusively energetically favorable. Therefore, given the opportunity, a PTR reaction process taken to completion will cause a highly charged precursor ion to continue to reduce its charge through consecutive charge reduction reactions until it is neutralized (and thereby lost from a mass spectrum). A less extreme possibility of this phenomenon is that an ion sub-population of a single initial charge state will be redistributed over several lower charge states following PTR, thereby effectively attenuating the signal of that molecular ion in a somewhat undesirable way.

To reduce or eliminate such spectral attenuation, a supplementary technique, known as "ion parking", can be employed in conjunction with the PTR reaction process to inhibit or greatly reduce the rate of reactions of specific charge states undergoing neutralization reactions. Ion parking uses supplementary or auxiliary oscillatory (AC) voltages applied to electrodes of an enclosing ion trap apparatus. The auxiliary AC voltage typically has a relatively low amplitude (on the order of 1 Volt) and is applied as a supplement to a main radio-frequency (RF) trapping voltage waveform that maintains containment of ions within the trap. As used in this document in reference to oscillatory resonance excitation voltages applied during ion parking, the term "frequency" does not refer to application of just a single-frequency oscillation but refers, instead, to the central frequency of a band of simultaneously applied frequencies (i.e., a frequency band), collectively having a band width. Similarly, a "waveform", as used herein in reference to ion parking, refers to simultaneous application of two or more of such frequency bands of various band widths. Noting the above definitions, a frequency of the oscillatory auxiliary voltage waveform is chosen so as to selectively match a frequency of motion of ions of a particular mass-to-charge (m/z) ratio within the trap (which in turn is determined by the main trapping field amplitude and the m/z ratio. The application of the auxiliary waveform thus selectively resonantly excites the motion of ions having the particular m/z ratio. The ions whose motion within the trap is resonantly excited in this fashion either experience slowed reaction kinetics or are generally inhibited from further charge reduction during the PTR reaction process. The ion parking procedure can thus consolidate the PTR product ions formed from the original variously protonated ions of any given protein molecule into a particular charge state or states at particular mass-to-charge (m/z) values during the reaction period. This technique is used to concentrate (or "park") the product ion signal into a single or limited number of charge states (and, consequently, into a single or a few respective m/z values) for higher sensitivity detection or further manipulation using collisional-activation, ETD, or other ion manipulation techniques. Various aspects of ion parking have been described in U.S. Pat. No. 7,064,317 B2 in the name of inventor McLuckey; U.S. Pat. No. 7,355,169 B2 in the name of inventor McLuckey; U.S. Pat. No. 8,334,503 B2 in the name of inventor McLuckey; U.S. Pat. No. 8,440,962 B2 in the name of inventor Le Blanc; and in the following documents: McLuckey et al., "Ion Parking during Ion/Ion Reactions in Electrodynamic Ion Traps", *Anal. Chem.* 2002, 74, 336-346; Reid et al., "Gas-Phase Concentration, Purification, and Identification of Whole Proteins from Complex Mixtures", *J. Am. Chem. Soc.* 2002, 124, 7353-7362; He et al., "Dissociation of Multiple Protein Ion Charge States Following a Single Gas-Phase Purification and Concentration Procedure", *Anal. Chem.* 2002, 74, 4653-4661; Xia et al., "Mutual Storage Mode Ion/Ion Reactions in a Hybrid Linear Ion Trap", *J. Am. Soc. Mass. Spectrom.* 2005, 16, 71-81; Chrisman et al., "Parallel Ion Parking: Improving Conversion of Parents to First-Generation Products in Electron Transfer Dissociation", *Anal. Chem.* 2005, 77(10), 3411-3414 and Chrisman et al., "Parallel Ion Parking of Protein Mixtures", *Anal. Chem.* 2006, 78, 310-316.

The technique known as "parallel ion parking", also discussed in the literature, is an extension to ion parking. The difference between ion parking and parallel ion parking is that, in the latter, ions within a broad m/z range (as opposed to a narrowly-defined range encompassing only one charge state of an protein of interest) are subjected to resonant excitation. Therefore, the m/z ratios of PTR reaction products are parked at a plurality of values corresponding to more than one charge state within the broad range. Despite the existence of a variety of described implementations of parallel parking in the literature, the technique consistently involves resonant excitation (radial in linear ion traps, axial in quadrupole ion traps) of the ions intending to be parked. It is possible to create a resonant excitation waveform that allows parking of PTR reaction product ions within a predetermined m/z range by either tailoring a unique waveform followed by inverse-Fourier transform techniques or by simply superimposing multiple single frequency waveforms simultaneously. In every case, the net result is to subject a precursor ion to PTR so as to cause a majority of ions to be redistributed over three to five charge states.

According to various methods in accordance with the present teachings, ions generated from PTR reactions, as described above, may be subjected to fragmentation by the technique of higher-energy dissociation (HCD). The HCD technique is a diagnostically powerful procedure that is used to energetically excite or activate (preparatory to fragmentation) all ions within a given m/z range, generally referred to as broad-band activation. In this method, ions can not only reach a minimum threshold for bond cleavage, but can also have additional energy imparted into them to reach higher energy dissociation thresholds. This is generally implemented through an axial acceleration of the ions in the presence of an electrical potential difference. The force exerted on each ion is a product of the charge, z, of that ion and the potential difference between two lens elements in the axial ion path. Because of this relationship, when ions encompassing a charge state distribution of the same molecular ion are subjected to HCD, those ions comprising a higher z will experience a greater force than those ions with a lower z, such that the higher-z ions may potentially dissociate through higher energy pathways. Conversely, the lower-z ions may remain partially intact, providing direct information for the molecular mass of the ion.

It has been found that, under similar activation conditions, proteins with differing charge states may dissociate differently from each other. Consequently, conventional selection of a single charge state for dissociation carries an inherent risk of poor dissociation due to the unknown fragmentation efficiency. By contrast, methods in accordance with the present teachings advantageously combine the PTR and HCD procedures so that ions derived from a single protein molecule and comprising a state envelope are fragmented. It is found by the inventors that the use of the combined PTR and HCD procedures is able to provide extensive sequence information—thereby minimizing the risk of poor dissociation from a single charge state—while potentially also maintaining information about the intact mass of the protein, thereby enhancing the likelihood of correctly identifying that protein. The benefits of the novel MS analysis methods taught herein are that the desired protein(s) are effectively purified through PTR and subsequently dissociated in such a way that the information content gained is more extensive than would be gathered from dissociation of a single charge state of the protein(s). Lastly, a high resolution, high mass accuracy mass spectrum may be produced following mass analysis in an accurate-mass analyzer, such as an Orbitrap™ mass analyzer.

Methods in accordance with the present teachings are especially useful for the analysis and identification of intact proteins having molecular weight in excess of 50 kDa. The inventors have discovered the surprising result that, taken together, the various advantageous factors noted above can enable accurate identification of multiple intact proteins or large peptides from even very complex mixtures derived from natural microorganism samples. Such identifications can enable microorganism identification to the species, subspecies or even strain level. The target protein or polypeptide ion single species or multiple species may be chosen so as to be indicative, based on prior knowledge or information, either individually or in combination, of the presence in a sample of a specific microorganism or cell type, or a specific strain or variant of a microorganism or cell type, or a given virulence factor or toxin, or of the capacity of a microorganism or cell to resist an antimicrobial compound or antibiotic drug.

The present invention, in one aspect, offers an alternative to traditional bottom-up proteomics methods, namely top-down analysis of intact proteins derived from microbial cells via a method which is applicable to substantially all microorganisms including Gram-positive bacteria, Gram-negative bacteria, mycobacteria, *mycoplasma*, yeasts, protozoans, filamentous (i.e., microscopic) fungi. The present invention may help to provide protein identification in complex mixtures, which in turn may help in the identification of microorganisms at the genus, species, subspecies, strain pathovar, and serovar level even in samples containing mixtures of microorganisms and/or microorganisms analyzed directly from pure and/or mixed cultures and from direct samples (e.g., surface swabs, bodily fluids, etc.). In addition, the approaches taught herein can be employed for targeted detection of virulence factors, antibiotic resistance and susceptibility markers, or other characteristics. The top-down methods of the present teachings are simple and quick because there is no need for chemical or enzymatic digestion of a sample and data processing is accomplished in real time.

Methods in accordance with the present teachings may comprise at least one or more of the following steps: microbial cell disruption, solubilization of proteins, sample clean-up (to desalt, remove insoluble components and debris, and/or concentrate), sample infusion or flow injection, fast partial liquid chromatographic separation, standard chromatographic separation, isoelectric focusing, ionization of proteins in solution, isolation of a given m/z range of the ions, causing the isolated range of ions to undergo PTR so as to form first-generation PTR product ions, optional isolation of an m/z range of the first-generation PTR product ions, optional mass spectrometry in MS or MS/MS mode, optionally causing the isolated range of first-generation PTR product ions to undergo a second PTR reaction so as to form second-generation PTR product ions, mass spectrometry in MS or MS/MS mode, and protein identification via molecular weight and/or protein sequence analysis, or using any statistical classification method. Preferably, but not necessarily, the mass spectrometry steps are performed with a high-resolution, high-accuracy mass spectrometer, such as a mass spectrometer comprising an Orbitrap™ mass analyzer.

BRIEF DESCRIPTION OF DRAWINGS

To further clarify the above and other advantages and features of the present disclosure, a more particular description of the disclosure will be rendered by reference to specific embodiments thereof, which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 4A is a mass spectrum of ions derived from a solution of ubiquitin containing abundant polymeric contaminants;

FIG. 4B is a mass spectrum of ions comprising a multiply protonated ubiquitin molecule of charge state +13 after m/z isolation from the population of ions depicted in FIG. 4A;

FIG. 5B is a mass spectrum of ions remaining after m/z isolation of the ion population depicted in FIG. 5A within a 2 Th-wide isolation window around 808 m/z, said isolation window encompassing multiply-protonated myoglobin ions having charge state +21;

FIG. 6E is a mass spectrum of ions generated from the charge-state +20 myoglobin ions, as depicted in FIG. 6D, by further reaction with PTR reagent for 1 millisecond without application of ion parking so as to produce multiply protonated myoglobin molecules having a range of charge states;

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the claims. The particular features and advantages of the invention will become more apparent with reference to the appended FIGS. 1, 2, 3A-3D, 4A-4D, 5A-5F, 6A-6G and 7 taken in conjunction with the following description.

Figure 1:
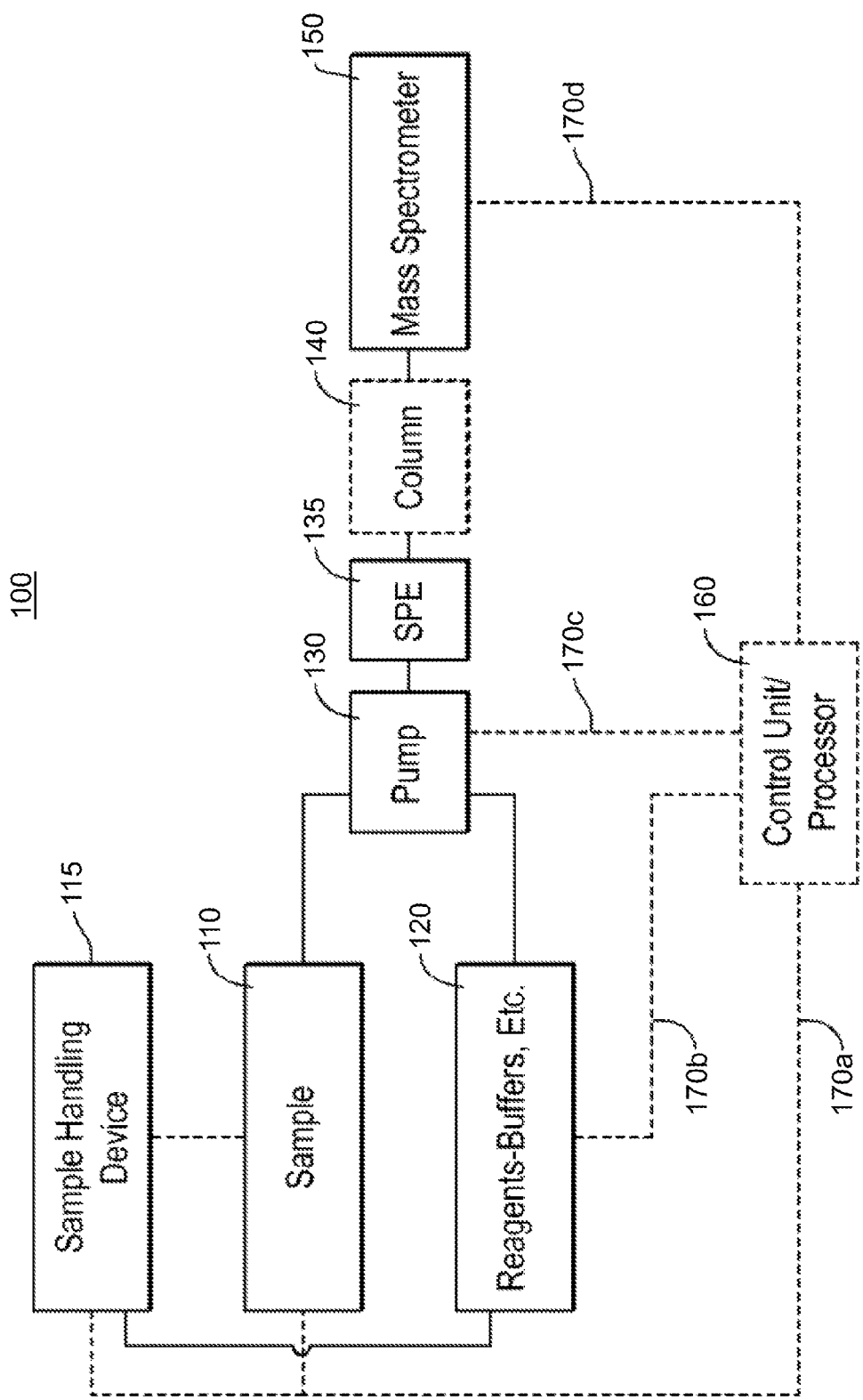
FIG. 1 is a block diagram schematically illustrating a system for rapid extraction and analysis of soluble proteins from at least one microorganism for identifying the at least one microorganism.

Referring now to FIG. 1, a system 100 for extraction of proteins from one or more microorganisms, detection of the proteins, and identification of the one or more microorganisms is schematically illustrated. The system 100 includes a sample handling device 115, a sample 110 that is accessible by the sample handling device 115, and sources of reagents, buffers, and the like 120, these sources being fluidly coupled to the sample handling device 115 by various tubing or other transfer lines. The system 100 further includes a first and, optionally, a second sample-purification device 135 (such as a solid phase extraction cartridge) configured for cleaning up samples (e.g., desalting, removing contaminants, concentrating proteins) and an optional chromatography column 140 that may be configured for at least partially purifying a sample 110 by liquid chromatography prior to mass-spec analysis. At least one sample-purification device 135 can comprise an in-line size exclusion chromatography column that can be used to not only remove salts but small molecules and lipids as well. The sample 110, the first and optional second sample-purification devices 135, and the optional chromatography column 140 are in fluid communication with a fluid handling pump 130, the various reagents, buffers and other fluids 120, and a mass spectrometer 150.

The sample handling device 115 is capable of preparing a range of sample types containing one or more microbes and delivering a soluble protein fraction extracted from the microbes to the mass spectrometer 150 for analysis. A sample 110 may be of any type suspected to contain one or more microorganisms including, without limitation, isolated colonies from a culture plate, cells from liquid growth medium, blood, blood culture, saliva, urine, stool, sputum, wound and body site swabs, soil, food, beverage, water, air, and environmental surface swabs.

The sample handling device 115 may include one or more of a cell disruption means, a robotic liquid handling means, a centrifuge, filtration means, an incubator, mixing means, a vacuum pump, a fluid pump, and reagents 120 that can be used for disruption of microbes and isolation of a soluble protein fraction. Disruption of bacterial, fungal, *mycoplasma* cells, viruses, and the like may be achieved by mechanical, chemical, enzymatic and other means as are commonly known in the art. Mechanical approaches include bead beating, use of pressure like French press and the like, sonication or other methods known in the art. Chemical methods include exposure to chaotropes such as urea, thiourea, or guanidine HCL to lyse the microbial cells and solubilize their contents. Alternatively, organic acid/solvents mixtures may be utilized to disrupt cells. Enzymatic methods include using lysozyme, lysostaphin or other lytic enzymes to form "holes" in the bacterial cell walls that allow the contents to leak out into the surrounding solution.

As illustrated in FIG. 1, the system 100 further includes an optional control unit 160 that can be linked to various components of the system 100 through linkages 170a-170d. For example, the control unit 160 can be linked to the sample 110 to control sample application, the reagents 120 to control the application of various reagents, the pump 130 to control fluid handling, flow rates, etc., to the sample handling device 115 to control sample preparation, and to the mass spectrometer 150 to control mass spectrometry parameters. In the illustrated embodiment, the control unit 160 can also serve as a data processing unit to, for example, process data from the mass spectrometer 150 or to forward the data to server(s) for processing and storage (the server is not shown in FIG. 1). Control unit 160 can also determine molecular weights and charge states of any generation of PTR product ions for MS/MS, MS$^n$, or molecular weight determination in real time. The Control Unit 160 can also be used to automatically forward the results to health care professionals.

In some embodiments, the system 100 is designed to be used by a clinician or a general laboratory technician who is not necessarily expert in all aspects of sample preparation, LC-MS operations, LC-MS methods development, and the like. As such, the control unit 160 can be designed to encapsulate the data system environment by providing a user with a simplified application interface that can be used to initiate and monitor essentially all aspects of assaying a sample 110 without requiring the user to interact with the overall hardware and control systems of the system 100. The control unit 160 is therefore configured to provide a degree of separation between the user and the underlying services that control devices, data files and algorithms for translating data to a user readable form. That is, the control unit 160 eliminates the need for the user to be aware of or in control of hardware for analyzing clinical samples and provides a simplified interface to send and receive information from the mass spectrometer.

The control unit 160 may be configured to internally monitor each sample analysis request and is capable of tracking the analysis request from start to finish through the system 100. Once data for a sample 110 is being acquired or has been acquired by the system 100, the control unit 160 may be configured to automatically start post processing the data based on the type of assay selected by the user. Most importantly, the control unit 160 can be configured to process data in real time during the acquisition process. Here results are returned to the user in real-time that include microbial identification, virulence and resistance characterization, strain matching information, and data on antibiotic susceptibility testing. Moreover, the control unit 160 can be configured to automatically select post-processing parameters based on the type of assay selected by the user, further reducing the need for the user to interact with the system once the assay has been selected and started for analysis. The control unit 160 can be designed as a layer that fits between the system 100 and the user to reduce the complexity needed to set up sample assays for acquisition. The control system 160 can also be configured to return only the most relevant data to the user to avoid overwhelming the user with extraneous information.

In one embodiment, the system 100 can further include a sample detection device (not pictured) operably coupled to or integrated with the sample handling device 115. The sample detection device can work with the sample handling device 115 or independently of the sample handling device 115 perform at least one of the following functions: i. identify samples entering the system; ii. identify assay types for the samples entering the system; iii. select an assay protocol based on the anticipated assay type and/or analyte of interest; iv. direct the sample handling device and/or the control system to initiate analysis of the analyte of interest in the sample; v. direct the control system to select one or more reagents based upon the assay protocol selected for the type of assay and/or analyte of interest; vi. direct the control system to select a liquid chromatography mobile phase condition based upon the assay protocol selected for the type of assay and/or analyte of interest and cause the liquid chromatography system to perform the assay and/or purify the analyte of interest; vii. direct the control system to select a mass spectrometer setting based upon the assay protocol selected for the assay type and/or analyte of interest and cause the mass spectrometer to create mass spectral data associated with the selected assay type and/or analyte of interest; and viii. direct the control system to analyze the mass spectral data associated with the selected assay type and/or analyte of interest to identify the presence and/or concentration of the analyte of interest.

The sample, or the processed sample, may be cleaned up and or purified prior to analysis by mass spectrometry. Such purification, or sample clean-up, may refer to a procedure that removes salts or lipids from the crude cell extract, or to a procedure that enriches one or more analytes of interest relative to one or more other components of the sample. It also may refer to sample processing and clean-up in a separate laboratory that has biosafety level-three facilities for handling mycobacteria or filamentous fungi. In this embodiment samples are transferred to the system and can be analyzed as described previously. In one embodiment, such purification, or sample clean-up, may be accomplished by a solid phase extraction device, in-line size exclusion chromatography and/or the optional chromatography column 140.

In one embodiment, the first and/or second sample-purification device 135 may include a solid phase extraction (SPE) cartridge. In some embodiments, the SPE cartridge may be in line directly with the high resolution/high mass accuracy mass spectrometer 150. In one embodiment, the SPE cartridge may be a polypropylene tip with a small volume of silica or other sorbent containing bonded $C_4$, $C_8$ or $C_{18}$ or other functional groups immobilized in the cartridge, for example, a StageTip™ cartridge (Thermo Fisher Scientific). In alternative embodiments, polymeric sorbents or chelating agents may be used. The bed volume may be as small as 1 μL or less but greater volumes may also be used. The apparatus and method are well suited to the complex samples derived from the microbial cells because each SPE cartridge is used only once, minimizing carryover problems from one sample to another.

In one embodiment, a sample-purification device 135 may be an in-line size-exclusion chromatography column designed to remove salts, small molecules, and lipids from the sample 110. The approach can be used to separate medium and large molecular weight proteins as well. Phases are selected to be compatible with partial (i.e., less than 100 percent) organic solutions and organic acids. Phases can accommodate protein size distributions that differ in molecular weight from $10^3$ to $10^8$ Da. Flow rates are adjusted in real time to effect separation of intact proteins from small molecules with separation flow rates typically much less than the higher flow rates used to remove small molecules, lipids, and salts from the system. In this embodiment, a sample-purification device 135 may also be heated to facilitate faster diffusion rates for intact proteins, thus significantly shortening run times. The flow of mobile phase through a sample-purification device 135 may also be diverted during a portion of the clean-up process to remove certain impurities from the flow stream and prevent them from entering the mass spectrometer 150.

In one embodiment, the optional chromatography column 140 may include a column configured for at least partial chromatographic separation of the proteins in the sample. The stationary phase in the chromatography column may be porous or non-porous silica or agarose particles, or a monolithic material polymerized or otherwise formed inside the column. The stationary phase may be coated with an appropriate material such as $C_{18}$, $C_8$, $C_4$ or another suitable derivative, or contain cation exchanger or other material, or the combination of the above to facilitate the separation of the proteins, and such material may be chemically bonded to the particles or monolith inside the column. Particle sizes typically range from about 1.5 μm to 30 μm. Pore sizes can range from 50 to 300 angstroms. Inside diameters of columns typically range from about 50 μm to 2.1 mm, and column length from about 0.5 cm to 25 cm, or other. The mobile phase or eluent may be a pure solvent, or a mixture of two or more solvents, and may contain added salts, acids and/or other chemical modifiers. The proteins are separated on the column based on one or more physiochemical properties, including size, net charge, hydrophobicity, affinity, or other physiochemical properties. Chromatographic separation methods include one or more of ion exchange, size exclusion, HILIC, hydrophobic interaction, affinity, normal-phase, or reverse-phase chromatography.

Additional methods of purifying the samples may include, without limitation, liquid chromatography, HPLC, UHPLC, precipitation, solid-phase extraction, liquid-liquid extraction, dialysis, affinity capture, electrophoresis, filtration, ultra-filtration or other suitable methods known in the art for purification.

Various methods have been described involving the use of HPLC for sample clean-up prior to mass spectrometry analysis. One of skill in the art can select HPLC instruments and columns that are suitable for use in the invention. The chromatographic column typically includes a medium (i.e., a packing material) to facilitate separation of chemical moieties in space and time. The medium may include very small particles, which may have a bonded surface that interacts with the various chemical moieties to facilitate separation of the analytes of interest. One suitable bonded surface is a hydrophobic bonded surface such as an alkyl bonded surface. Alkyl bonded surfaces may include $C_4$, $C_8$, or $C_{18}$ bonded alkyl groups. In addition, monolithic and other phases known in the state of the art may be used as well. The chromatographic column includes an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used sequentially or as a two-dimensional (2D) chromatography system wherein a test sample may be applied to a first column at the inlet port, eluted with a solvent or solvent mixture onto a second column, and eluted with a solvent or solvent mixture from the second column to the outlet port. Different solvent modes may be selected for eluting the analytes. For example, liquid chromatography may be performed using a gradient mode, an isocratic mode, or a polytypic (i.e. mixed) mode.

Figure 2:
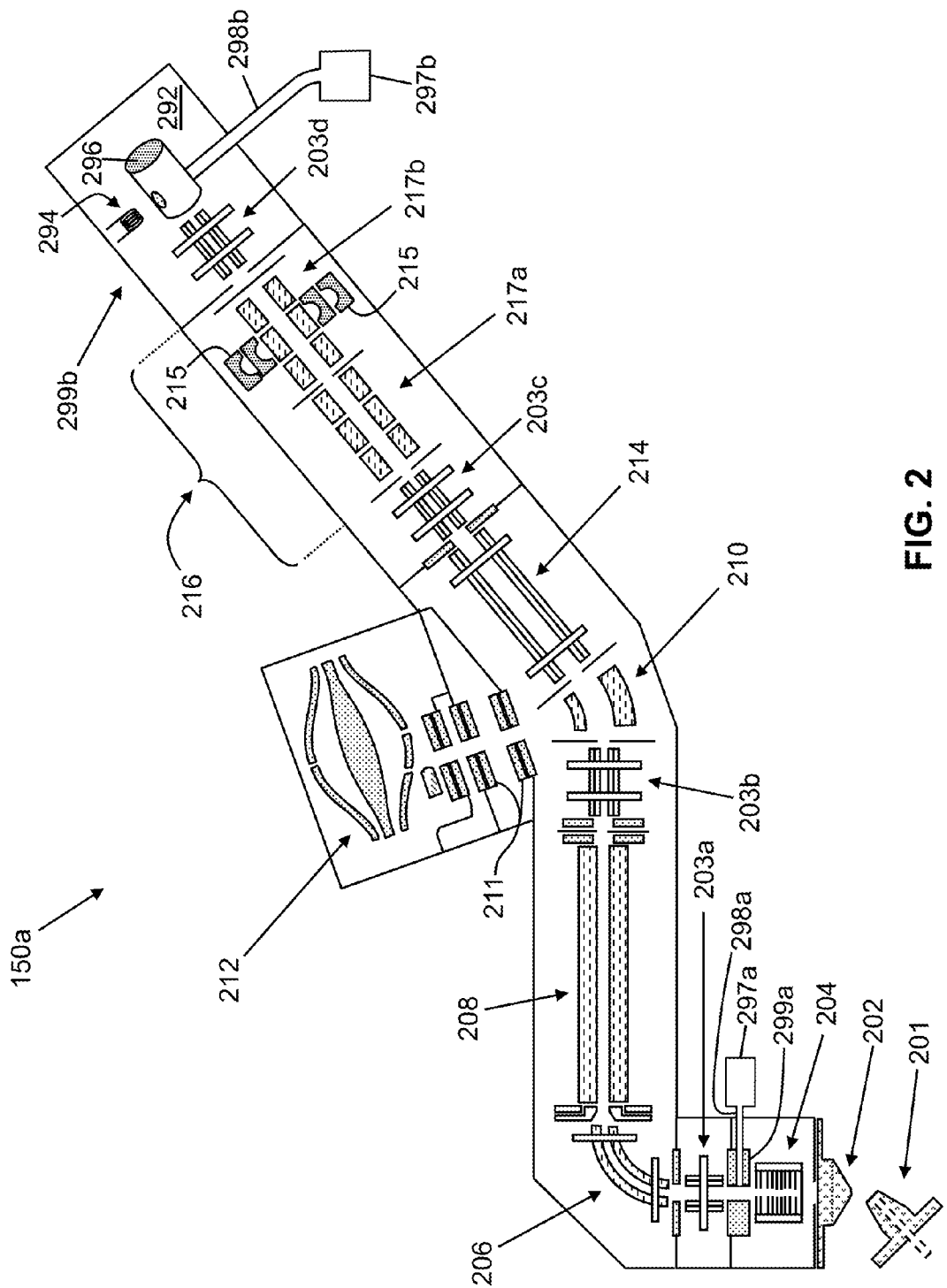
FIG. 2 is a schematic representation of an exemplary mass spectrometer suitable for employment in conjunction with methods according to the present teachings, the mass spectrometer comprising a hybrid system comprising a quadrupole mass filter, a dual-pressure quadrupole ion trap mass analyzer and an electrostatic trap mass analyzer.

FIG. 2 is a schematic depiction of an exemplary mass spectrometer 150a which may be employed as the mass spectrometer 150 of FIG. 1. The mass spectrometer illustrated in FIG. 2 is a hybrid mass spectrometer, comprising more than one type of mass analyzer. Specifically, the mass spectrometer 150a includes an ion trap mass analyzer 216 as well as an Orbitrap™ analyzer, which is a type of electrostatic trap mass analyzer. Since, as will be described below, various analysis methods in accordance with the present teachings employ multiple mass analysis data acquisitions, a hybrid mass spectrometer system can be advantageously employed to improve duty cycles by using two or more analyzers simultaneously. The Orbitrap™ mass analyzer 212 employs image charge detection, in which ions are detected indirectly by detection of an image current induced on a set of electrodes by the motion of ions within the electric fields of the mass analyzer. In the widely used data-dependent experimental scheme, an initial "survey" scan is used to identify interesting features eluting from a liquid chromatograph (LC) and, subsequently, several (in the range of 10-50) "dependent" mass scans—which may comprise tandem mass spectral scans (MS")—are performed to interrogate the precursor species identified in the survey scan. If the instrument is a hybrid type, having more than one type of mass analyzer, then the duty cycle can be increased by using one analyzer for the survey scan, and another for the dependent MSn scans.

In operation of the mass spectrometer 150a, an electrospray ion source 201 provides ions of a sample to be analyzed to an aperture of a skimmer 202, at which the ions enter into a first vacuum chamber. After entry, the ions are captured and focused into a tight beam by a stacked-ring ion guide 204. A first ion optical transfer component 203a transfers the beam into downstream high-vacuum regions of the mass spectrometer. Most remaining neutral molecules and undesirable high-velocity ion clusters, such as solvated ions, are separated from the ion beam by a curved beam guide 206. The neutral molecules and ion clusters follow a straight-line path whereas the ions of interest are caused to bend around a ninety-degree turn by a drag field, thereby producing the separation.

A quadrupole mass filter 208 of the mass spectrometer 150a is used in its conventional sense as a tunable mass filter so as to pass ions only within a selected narrow m/z range. A subsequent ion optical transfer component 203b delivers the filtered ions to a curved quadrupole ion trap ("C-trap") component 210. The C-trap 210 is able to transfer ions along a pathway between the quadrupole mass filter 208 and the ion trap mass analyzer 216. The C-trap 210 also has the capability to temporarily collect and store a population of ions and then deliver the ions, as a pulse or packet, into the Orbitrap™ mass analyzer 212. The transfer of packets of ions is controlled by the application of electrical potential differences between the C-trap 210 and a set of injection electrodes 211 disposed between the C-trap 210 and the Orbitrap™ mass analyzer 212. The curvature of the C-trap is designed such that the population of ions is spatially focused so as to match the angular acceptance of an entrance aperture of the Orbitrap™ mass analyzer 212.

Multipole ion guide 214 and optical transfer component 203b serve to guide ions between the C-trap 210 and the ion trap mass analyzer 216. The multipole ion guide 214 provides temporary ion storage capability such that ions produced in a first processing step of an analysis method can be later retrieved for processing in a subsequent step. The multipole ion guide 214 can also serve as a fragmentation cell. Various gate electrodes along the pathway between the C-trap 210 and the ion trap mass analyzer 216 are controllable such that ions may be transferred in either direction, depending upon the sequence of ion processing steps required in any particular analysis method.

The ion trap mass analyzer 216 is a dual-pressure linear ion trap (i.e., a two-dimensional trap) comprising a high-pressure linear trap cell 217a and a low-pressure linear trap cell 217b, the two cells being positioned adjacent to one another separated by a plate lens having a small aperture that permits ion transfer between the two cells and that presents a pumping restriction and allows different pressures to be maintained in the two traps. The environment of the high-pressure cell 217a favors ion cooling, but also favors ion fragmentation under controlled conditions by either collision-induced dissociation or electron transfer dissociation or ion-ion reactions such as proton-transfer reactions. The environment of the low-pressure cell 217b favors analytical scanning with high resolving power and mass accuracy. The low-pressure cell includes a dual-dynode ion detector 215.

The use of either a step of electron transfer dissociation or proton transfer reaction within a mass analysis method requires the capability of causing controlled ion-ion reaction within a mass spectrometer. Ion-ion reactions, in turn, require the capabilities of generating reagent ions and of causing the reagent ions to mix with sample ions. The mass spectrometer 150a, as depicted in FIG. 2, illustrates two alternative reagent-ion sources, a first reagent-ion source 299a disposed between the stacked-ring ion guide 204 and the curved beam guide 206 and a second reagent-ion source 299b disposed at the opposite end of the instrument, adjacent to the low-pressure cell 217b of the linear ion trap mass analyzer 216. Generally, any particular system will only include one reagent ion source at most. However, two different reagent ion sources are depicted and discussed here for illustrative purposes. Although the following discussion is directed to reagent ion sources for PTR, similar discussion may apply to ETD reagent ion sources.

A first possible reagent ion source 299a may be located between the stacked ring ion guide 204 and the curved beam guide 206. The reagent ion source 299a comprises a glow discharge cell comprising a pair of electrodes (anode and cathode) that are exposed to a reagent gas conduit 298a that delivers the reagent gas from a reagent liquid (or solid) reservoir 297a having a heater that volatilizes the reagent compound. When a high voltage is applied across the electrodes, glow discharge is initiated which ionizes the reagent flowing between the electrodes. Reagent anions from the glow discharge source are introduced into the ion optics path ahead of the quadrupole mass filter 208 within which they may be m/z selected. The reagent ions may then be accumulated in the multipole ion guide 214, and subsequently transferred into the high pressure cell 217b of the dual-pressure linear ion trap 216 within which they are made available for the PTR reaction. The reaction products may be directly transferred to the low pressure cell 217a or to the Orbitrap™ mass analyzer 212 for m/z analysis.

A possible alternative reagent ion source 299a may be located adjacent to the low pressure linear trap cell 217b where it may comprise an additional high-vacuum chamber 292 from which reagent ions may be directed into the high pressure cell 217b through an aperture in between chamber 292 and the high-pressure cell. In operation, gaseous reagent compound is supplied from a reagent liquid (or solid) reservoir 297b having a heater that volatilizes the reagent compound and is directed through a reagent gas conduit 298b that delivers the reagent gas into a partially confined ion generation volume 296. In operation, thermionic electrons supplied from an electrically heated filament 294 are directed into the ion generation volume 296 with a certain pre-determined energy by application of an electrical potential between the filament 294 and an accelerator electrode (not shown). The supplied energetic electrons cause ionization of the reagent gas so as to generate reagent ions. The reagent ions may then be guided into the high pressure cell 217b by ion optical transfer component 203a under the operation of gate electrodes (not shown).

Figure 3A:
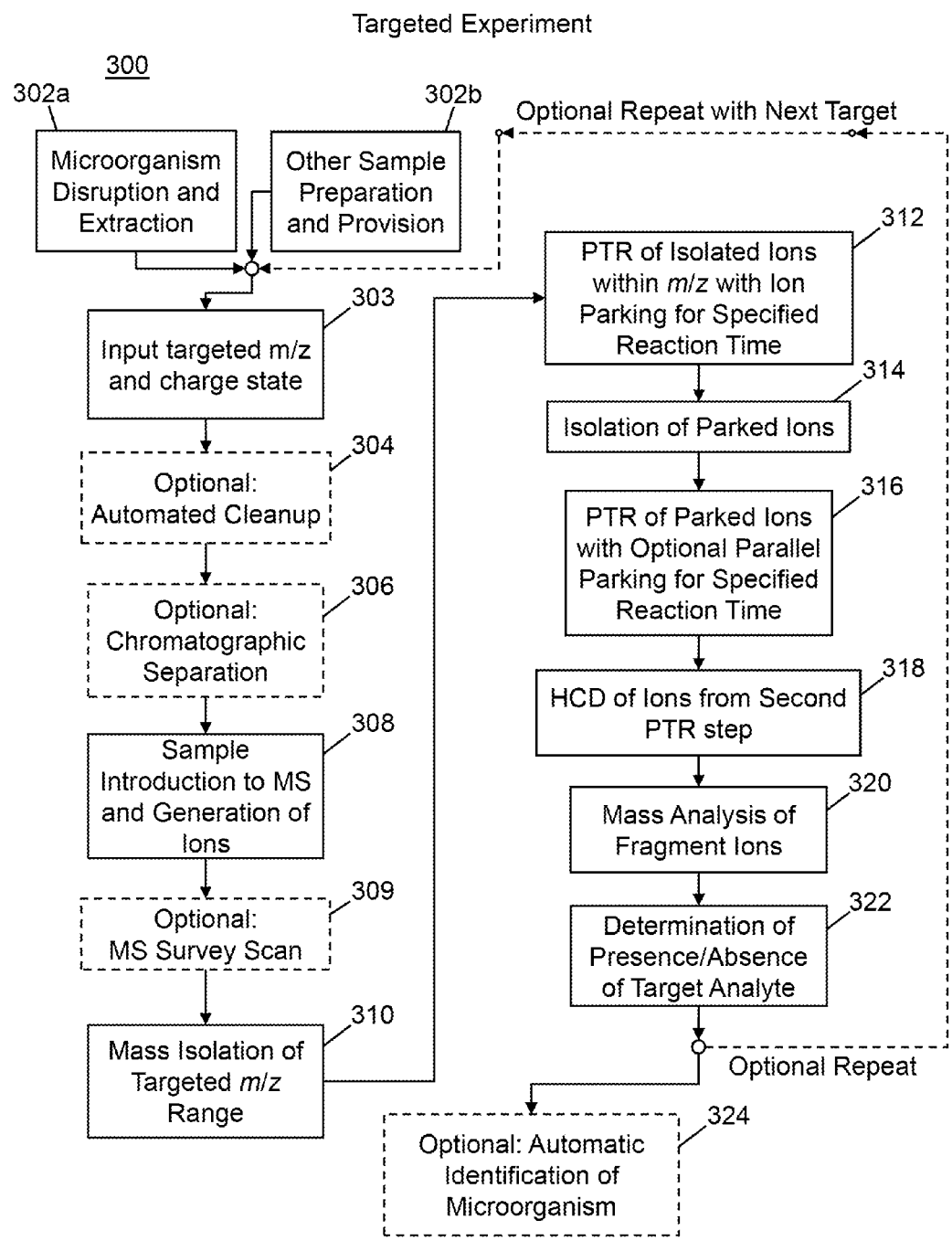
FIG. 3A is a schematic flow chart of a first exemplary method in accordance with the present teachings, said first method directed towards determining the presence and/or concentration of or absence of a target protein analyte.

Exemplary methods in accordance with the present teachings are schematically illustrated in the flow diagrams shown in FIGS. 3A-3D. FIG. 3A schematically illustrates a first such exemplary method, method 300, for monitoring for the presence of and, optionally, quantifying, certain specific targeted analyte proteins in a sample. The initial step 302a (or alternatively, step 302b) is a sample preparation and provision step. Step 302a includes microorganism disruption (e.g., lysis) and extraction, in case the sample is derived from, for example, a bacterial colony. In a targeted analysis, such as is outlined in FIG. 3A, certain information relating to the analyte's mass spectral signature (such as one or more specific diagnostic ion species) is known beforehand. The known information will generally include the analyte's molecular weight. Accordingly, the m/z values of various charge states of ions generated from the molecule (e.g., variously multiply protonated versions of the analyte molecule as produced during electrospray ionization) will likewise be known. Generally, the m/z values of diagnostic fragment ions produced during fragmentation reactions of the ions will also be known. Thus, in step 303, one or more predetermined mass-to-charge ratios $(m/z)_p$ and corresponding charge states ($z_p$) pertaining to such specific ions to be searched for are input to a control program or control unit, such as control unit or processor 160 (FIG. 1). Assuming that each targeted ion is formed by protonation of an analyte molecule in an ion source, then, for each such specific ion, the number of adducted protons is given by $z_p$ and the molecular weight, MW, of the compound from which the ion was formed is given by $MW=[z_p \times (m/z)_p] - n \times M_{proton}$, where n is a small integer (e.g., 1≤n≤5) and $M_{proton}$ is the mass of a proton, in atomic units (AU).

The next steps 304 and 306 of the method 300 are the steps of solid-phase clean-up, or size-exclusion chromatography and chromatographic separation, respectively, as described above. In some experimental situations, the extracted sample may be directly infused into a mass spectrometer in the subsequent sample introduction step 308; thus, the steps 304 and 306 are shown by dashed lines as being optional. As an alternative to performing the steps 304 and 306, samples may also be at least partially purified during "offline" during the sample preparation step 302b using approaches including dialysis, or other techniques known in the state of the art.

When an analysis must be completed according to time constraints, as in some clinical applications, the required time for the analysis may be shortened by employing either a SPE step 304, a time-compressed chromatography step as described in U.S. Pat. No. 5,175,430 to inventor Enke, or the method of "Fast Partial Chromatographic Separation" (FPCS) in the chromatography step 306 as described in international (PCT) patent application publication WO 2013/166169 A1. Generally, in performing FPCS, a crude extract of microbial cells containing a complex mixture of various organic and inorganic analytes (small organic molecules, proteins and their naturally occurring fragments, lipids, nucleic acids, polysaccharides, lipoproteins, etc.) is loaded on a chromatographic column and subjected to chromatography. However, instead of allowing a gradient to elute each analyte separately (ideally, one analyte per chromatographic peak), the gradient is intentionally accelerated to the extent that substantially no chromatographic peaks obtained for example approximately eight minutes or less, and preferably five minutes or less instead of a much longer run time that would be required to obtain a baseline separation. In the FPCS separation, many analytes are intentionally co-eluted from the column at any given time according to their properties and the type of chromatography (reverse phase, HILIC, etc.) used. Partial or incomplete separation may be also accomplished by other methods known to one skilled in the art, including but not limited to the use of mobile phase solvents and/or modifiers that reduce retention of compounds on the column, selection of stationary phase media that reduce retention of compounds on the column (including particle size, pore size, etc.), operation of the chromatographic system at higher flow rate, operation of the chromatographic system at an elevated temperature, or selection of a different chromatographic separation mode (i.e., reversed-phase, size exclusion, etc.). The FPCS technique yields few or, possibly, no resolved chromatographic peaks across the whole gradient. Thus, substantially the only relevant information derived from a chromatogram is the time of elution from the column. Each mass spectrum that is recorded represents a "subset" of co-eluting analytes that is then ionized, separated in the mass analyzer and detected.

In step 308 (FIG. 3A), the sample is introduced into a mass spectrometer and the sample is ionized. The sample may be provided as the eluate material that emerges from an SPE cartridge, a chromatography apparatus or, alternatively, by direct infusion of the eluate solution. Upon being provided to the mass spectrometer, the sample compounds are ionized (step 308) by an electrospray ionization source of the mass spectrometer. These electrospray-generated ions are herein referred to as "original" ions. At this juncture, a full or segmented $MS^1$ scan may optionally be performed (step 309) in order to identify the protein-rich regions in m/z space. (Note that in this document, the term "scan" may be taken to generally refer to a mass spectrum when used as a noun or, alternatively, to the acquisition of a mass spectrum, when used as a verb). The survey scan will generally encompass a certain experimental range, $\Delta(m/z)_{survey}$, of mass-to-charge ratios. In the case of a targeted analysis, as is outlined in the method 300 (FIG. 3A), the $MS^1$ scan may be unnecessary and execution of the method 300 may proceed directly to step 310, in which a subset of the ions is then isolated for further reaction and analysis. The isolation performed in step 310 may be such that ions within a certain pre-determined m/z range or possibly multiple pre-determined m/z ranges are retained for the subsequent reaction and analysis whereas ions outside the pre-determined m/z range or ranges are discarded. The pre-determined m/z range or ranges are set so as to correspond to the input m/z ratios (step 303) of the targeted analyte proteins or peptides whose presence or quantity is detected or monitored in the execution of the method.

Generally, the isolation of step 310 may be performed, in known fashion, by introducing the ions from the ion source into an ion trap—such as a three-dimensional ion trap, a curved ion trap (sometimes referred to as a "C-Trap") a single segment linear ion trap, multiple segmented linear ion trap, multipole ion guide or quadrupole mass filter—and then resonantly ejecting the ions whose m/z ratios are outside of the desired range by applying a supplemental AC voltage across pairs of electrodes of the ion trap or applying the appropriate RF/DC voltage ratios to isolate the ion population of interest. In some embodiments, the frequency of the supplemental voltage may be swept through various frequencies such that the ions are ejected in sequence according to their m/z ratios. In some embodiments, the combination of superimposed frequencies may be provided with multiple segments of missing frequencies (i.e., "notches") such that ions comprising two or more non-contiguous m/z ratio ranges are simultaneously isolated within the trap.

A quadrupole mass filter may also (or alternatively) be used to isolate the defined or targeted mass ranges of interest. Particular m/z ranges of the original ions are selected by a single or series of fixed RF/DC voltage ratios in order to select the appropriate mass isolation windows. The instrumental configuration employed in this case may be a hybrid mass spectrometer instrument comprising a quadrupole, a C-trap, an Orbitrap™ mass analyzer, and a high energy collision cell (HCD) where the isolated ion population can be stored in either the C-trap or HCD cell for PTR experiments. The isolated population or populations of the original ions may be considered to comprise "precursor" ions, because, subsequent to step 310, these ions are subjected to subsequent ion-ion reactions or to fragmentation.

In a preferred embodiment, the isolation of the precursor ion population may be performed in a first segment of a segmented linear ion trap. After isolation of the desired ion population, the multiply-charged protein ion population may be advantageously moved to another segment of the linear ion trap. These steps can be repeated multiple times for isolated defined ranges of precursor ions prior to the PTR process.

Step 312 of the method 300 (FIG. 3A) is a PTR step that includes ion parking. In the PTR procedure, anions are generated using either a rhenium-based filament with chemical ionization or glow discharge ionization source from a suitable high electron affinity based gaseous reagent. Chemical ionization can be performed using nitrogen, methane, isobutane, or other known gases in the state of the art. The anion reagent may be a gas at room temperature or may be a liquid with sufficient vapor pressure to produce an excess of anions which will drive the PTR process under pseudo-first order reaction conditions. The anions are then transferred from the source region to the segmented linear trap whereby the specific anion reagent is mass isolated using supplemental AC voltages as described above. The anion source can be in-line with the electrospray source or mounted on the opposite end of the segmented linear ion trap. Alternatively, a quadrupole mass filter can perform the anion isolation as well with the subsequent PTR process occurring in the C-trap or HCD cell of the instrument.

The execution of step 312 includes applying a supplemental AC excitation waveform across a pair of electrodes of an ion trap within which sample-derived cations are reacted with PTR reagent anions for a predetermined time period. The employment of this "ion parking" procedure concentrates the distribution of ions derived from any particular first-generation protein or polypeptide ion into a particular restricted range of m/z values, as determined by the applied waveform. This procedure will generally restrict the ions derived from any particular protein or polypeptide ion into a particular charge state, thereby simplifying a resulting mass spectrum and increasing the intensity of any mass spectral peaks corresponding to the particular protein or polypeptide. The particular range of m/z values into which the ions are restricted may comprise ions of different respective charge states derived from the first generation ion species. Generally, ions will be parked in a charge state that is a few units less (for example, not more than five units less) than the charge state, $z_p$, of the initially targeted precursor ions. Accordingly the applied waveform(s) used for ion parking will have a frequency that matches a frequency of motion of ions that have a mass-to-charge ratio, $(m/z)_2$, given by $$(m/z)_2 = (m_p - n \times M_{proton})/(z_p - n) \qquad \text{Eq. 1}$$

where n is a small integer (e.g., $1 \leq n \leq 5$) and $M_{proton}$ is the mass of a proton, in atomic units (AU). Preferably, $(m/z)_2$ is greater than all of the mass-to-charge ratios encompassed by the isolation window employed in the prior step 310 so as to thereby optimize the separation of contaminant ions from ions corresponding to potential protein or polypeptide analytes.

The application of ion parking during step 312 causes analyte-derived ions to become spectrometrically separated from non-analyte or contaminant ions that may be co-isolated together with analyte ions during an earlier mass isolation step (e.g., step 310). Analyte ions, whose m/z ratios are such that the frequency of their trap oscillations correspond to an applied supplemental AC excitation frequency, are effectively removed from further charge-reduction reaction with PTR reagent ions whereas non-analyte ions of differing m/z ratios experience further charge reduction or even neutralization. In order to effect the mass spectrometric separation, the applied supplemental waveform is preferably chosen so as to cause a charge reduction of analyte ions by a small number of charge units—preferably, a charge reduction of one or two charge units—relative to the initially isolated charge state (step 310). If the degree of charge reduction is less than a single charge unit of the analyte, then analyte ions will not be "parked" but non-analyte ions may be parked undesirably; if the degree of charge reduction of analyte ions is too great, then the mass-to-charge ratio of analyte ions may be increased to a range that is out of the range of detection of a mass analyzer.

Because the analyte ions are spectrometrically separated from other ions in step 312, an additional isolation step according to m/z ratio (step 314) produces an essentially pure population of ions of the targeted analyte in a desired charge state (provided that such analyte ions are present in the sample). The isolated analyte ions in the charge-reduced state (relative to the charge state of analyte ions initially isolated in step 310) are here referred to, with regard to the method under discussion, as first-generation product ions. A second PTR step (step 316) applied to these purified first-generation product ions then produces a new distribution of ion species in a plurality of respective charge states, where each such ion species is derived from the targeted analyte. The distribution may include residual first-generation product ion species in addition to new species formed during the second PTR step 316, here referred to as second-generation product ion species. The degree of charge reduction depends on the amount of time during which analyte ions are allowed to react with PTR reagent ions. The actual reaction time may vary from as little as 1 ms to approximately 100 ms. With shorter reaction times, a residual quantity of the first-generation product ion species may remain. The step 316 may optionally include parallel parking so as to generate a plurality of ion species having respective charge states. In such cases, the applied auxiliary waveform used for ion parking will comprise a summed plurality of respective component waveforms (a total of n such component waveforms), each component waveform having a frequency, $F_j$, ($1 \leq j \leq n$) that matches a frequency of motion of a respective reduced-charge-state ion species that has a mass-to-charge ratio, $(m/z)_j$, ($1 \leq j \leq n$) given by $$(m/z)_j = (m_p - j \times M_{proton})/(z_p - j) \qquad \text{Eq. 2}$$

where $M_{proton}$ is the mass of a proton, in atomic units (AU). Each $(m/z)_j$ may be greater than all of the mass-to-charge ratios encompassed by the isolation window employed in the prior step 314 so as to further enhance the separation contaminant ions from ions corresponding to potential protein or polypeptide analytes.

The entire population of ion species that results from the PTR step 316 may be subjected to fragmentation using the technique of Higher collisional Energy Dissociation (HCD) in step 318. Because each and every ion species that remains after step 316 is, theoretically, derived from the targeted analyte, all such fragments may provide analyte-specific diagnostic information. Because, ions with differing charge states may dissociate differently from each other, the simultaneous fragmentation of ions having differing charge states may lead to richer diagnostic protein structural information (peptide sequence information) than fragmentation of a single charge state. During the fragmentation, the applied collision energy may be controlled so as to avoid over-fragmentation—in other words, further fragmentation of fragments. In the following step 320, the fragments are analyzed by a mass analyzer so as to generate a mass spectrum of the fragments. In step 322, the mass spectral data of the fragments may be employed to confirm the presence (or lack thereof) of the targeted analyte in the original sample. The intensity of observed mass spectral peaks relating to fragments may also be related to a quantity of the analyte in the sample.

In many situations, more than one targeted analyte may be searched for in a single sample. In such situations, the execution of the method 300 may return (dashed line labeled "optional repeat") back to step 303 or, depending on the sample and employed instrumentation, back to any of steps 304-310 in order to acquire data and make determinations pertaining to a different analyte. Finally, data pertaining to one or several analytes may be employed (step 324) to automatically identify a microorganism from which the sample was derived.

Figure 3B:
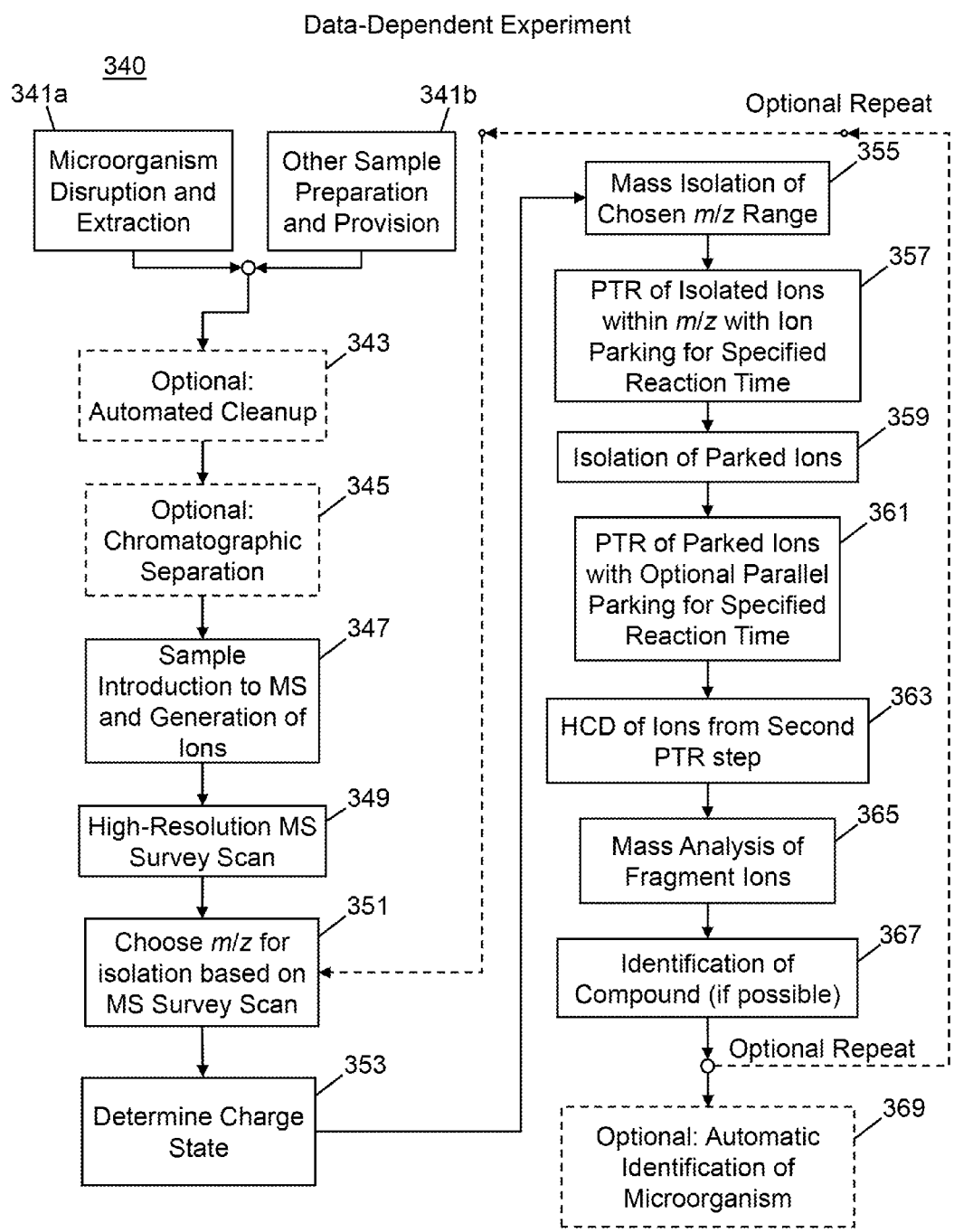
FIG. 3B is a schematic flow chart of a second exemplary method in accordance with the present teachings, said second method directed towards data-dependent determination of the presence and/or concentration of one or more proteins in a sample.

FIG. 3B is a schematic flow chart of a second exemplary method (method 340) in accordance with the present teachings. The method 340 is directed towards data-dependent determination of the presence and/or concentration of one or more proteins in a sample. As opposed to a targeted experiment (e.g., method 300) in which the identities of protein analytes to be searched for are known beforehand, the data-dependent experiment does not assume such knowledge. Instead, in the data-dependent experiment, the specific details of steps performed by a mass spectrometer are determined during the analysis itself, dependent upon data acquired during earlier steps of the same experiment. Accordingly, the method 340 does not include a data input step corresponding to step 303 of method 300 and the high resolution MS survey scan (step 349) is not optional, in contrast to the corresponding step 309 of method 300. Further, the choice of m/z ranges of original ions that are isolated (steps 351 and 355) depends on the results obtained in a prior survey scan (step 349), in contrast to the mass isolation step 310 of method 300 in which such m/z ranges are predetermined.

In other aspects, many steps of the method 340 (FIG. 3B) are similar or identical to corresponding steps of the method 300 (FIG. 3A). Accordingly, steps 341a, 341b, 343, 345, and 347 of the method 340 correspond to steps 302a, 302b, 304, 306 and 308, respectively, of the method 300. Similarly, steps 357, 359, 361, 363 and 365 of method 340 correspond to steps 312, 314, 316, 318, and 320, respectively, of method 300. Because of the similarities between the corresponding steps, the above-presented detailed discussions of such steps are not re-presented here.

The data-dependent method 340 is useful in situations in which the identities of compounds of interest are not known beforehand and in which each analyzed sample portion is of limited complexity, such that acquired survey data provides sufficient information to enable automatic determination of m/z ratio ranges to be investigated. The limited complexity of a sample portion may be related to a limitation of the number of chemical constituents in the sample portion, possibly as a result of prior highly-efficient sample clean-up (step 343) or highly-resolved chromatographic separation (step 345) being used to provide the sample portion.

In step 351 of the method 340 (FIG. 3B), an m/z range for isolation (i.e., an "isolation window") of original ions is chosen, based on the results of a prior survey scan of the original ions (step 349). In similarity to conventional data-dependent mass spectrometric analysis methods, the choice may be made based on the relative intensities of a limited number of mass spectral peaks observed in the survey scan. Specifically, if the survey scan mass spectrum consists primarily of a relatively small number (less than about 20) of well-resolved peaks that are significantly more intense than a spectral baseline, then each iteration of steps 351-367 (following the execution flow according to the dashed line labeled "optional repeat" in FIG. 3B) may correspond to choosing an isolation window encompassing each of these most-intense peaks.

Figure 7:
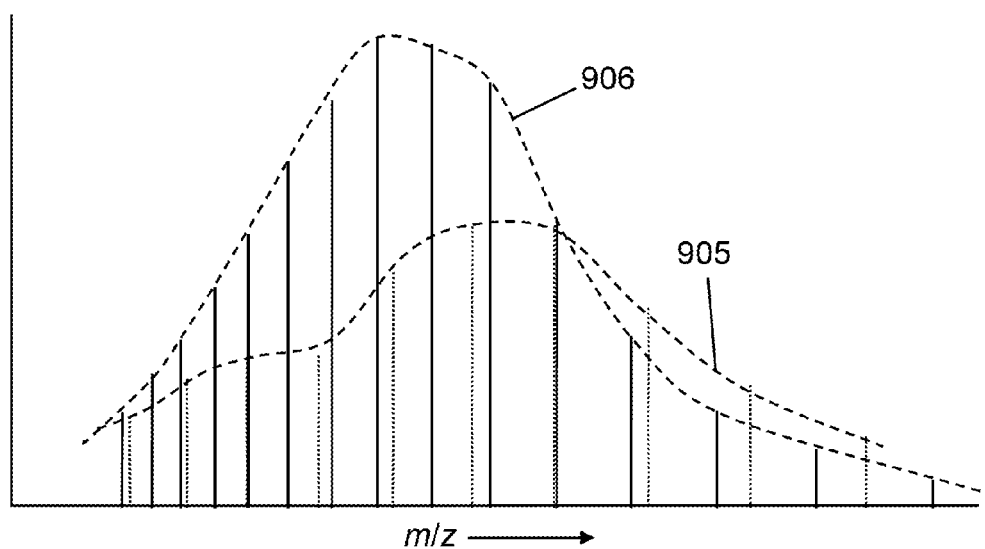
FIG. 7 is a schematic representation of two overlapping sets of mass spectral lines, each set comprising a charge state distribution of a different respective analyte.

A more sophisticated method of survey scan analysis that involves automated real-time mass spectral deconvolution has been described in co-pending and commonly assigned U.S. Provisional Application No. 62/132,124 filed on Mar. 12, 2015 in the names of inventors Yip et al. and titled "Methods for Data-Dependent Mass Spectrometry of Mixed Biomolecular Analytes", the disclosure of said application hereby incorporated by reference herein in its entirety. The aforementioned Provisional Application describes deconvolution procedures by which various sets of mass spectral peaks may be recognized, where each set of peaks corresponds to a single analyte as a charge state distribution. A schematic example, as illustrated in FIG. 7, illustrates how the deconvolution procedure, when incorporated into the step 351, may lead to recognition of two overlapping sets of lines, depicted by envelope 905 and envelope 906, respectively. With the information provided by this initial survey procedure, a single representative mass spectral line may be chosen from each set of lines when determining isolation windows for further analysis (step 351). This method avoids the potential for choosing isolation windows that yield redundant information using the conventional relative line intensity criterion.

In step 353 of the method 340 (FIG. 3B), the charge state of the mass-spectral line chosen for subsequent isolation (step 355) is determined, so that subsequent ion parking procedures (e.g., step 357) can employ excitation waveforms that correspond to correctly calculated reduced charge states. The charge state of the chosen line may be determined, if the survey scan includes resolved lines of isotopic variants, by the spacing of the lines of the isotopic variants. Alternatively, the charge state may be determined by application of the methods described in the aforementioned U.S. Provisional Application No. 62/132,124.

Step 367 of the method 340 (FIG. 3B) replaces step 322 of the method 300 (FIG. 3A) because there is no question pertaining to the "presence" of compounds for which mass spectral lines are known to exist. Instead, an attempt may be made, in step 367, to identify the compound corresponding to the line for which an isolation range was chosen in step 351, based on the m/z (step 351) and determined charge state, z (step 353), of the chosen line and the observed m/z values of the fragments (step 365). The compound determination may make beneficial use of annotated databases of mass spectral lines of first generation ions and of fragments. Finally, after all iterations of the loop of steps defined between step 351 and 367 have been completed, automatic identification of a microorganism from which the sample was derived may be made, if appropriate, if a sufficient number of diagnostic protein compounds have been identified.

Figure 3C:
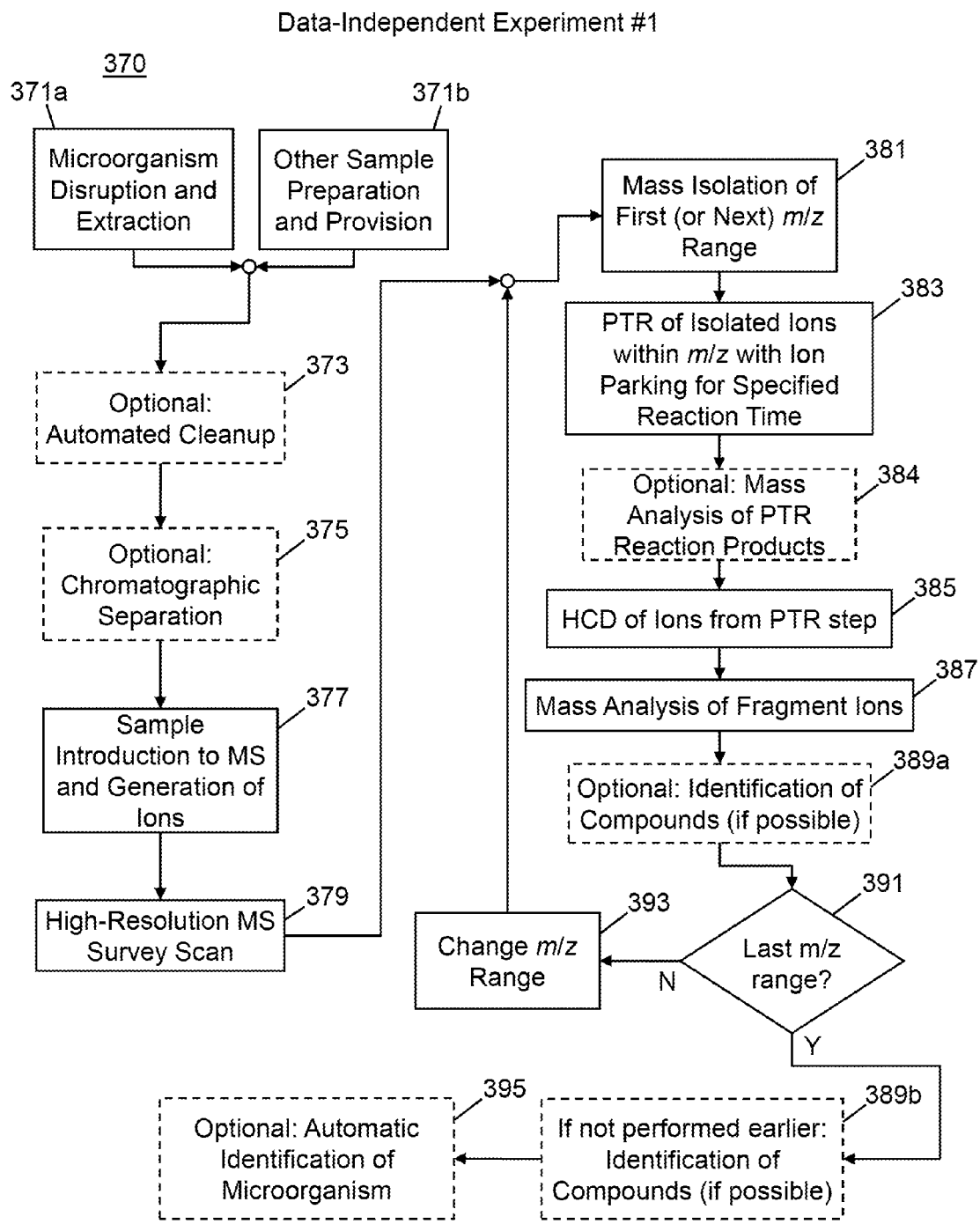
FIG. 3C is a schematic flow chart of a third exemplary method in accordance with the present teachings, said third method directed towards data-independent determination of the presence and/or concentration of one or more proteins in a sample.

FIG. 3C is a schematic flow chart of a third exemplary method in accordance with the present teachings. The method 370 illustrated in FIG. 3C directed towards data-independent determination of the presence and/or concentration of one or more proteins in a sample. The data independent method 370 illustrated in FIG. 3C (as well as the alternative data-independent method 400 illustrated in FIG. 3D) may be employed when no target analytes exist and when the spectrum is too complex (for example, many overlapping or unresolved lines, with few or no lines of dominant intensity) to employ a data-dependent analysis. The steps 371a, 371b, 373, 375, 377 and 379 of the method 370 (FIG. 3C) are similar to the respective corresponding steps 302a, 302b, 304, 306, 308 and 309 of the method 300 (FIG. 3A) and are thus not described in detail here.

After the execution of the High-Resolution MS Survey Scan step (379), the method 370 proceeds to repeatedly loop through the set of steps 381 through 393. During each execution of the set of steps 381 through 393, a respective m/z range is interrogated by performing the following steps: isolation of a respective sub-population of original ions within the respective interrogated m/z range (step 381), reaction of the isolated sub-population of ions with PTR reagent for a specified reaction time under the application of ion parking (step 383), optional mass analysis of the ions remaining after the PTR procedure (step 384), fragmentation of the ions remaining after the PTR procedure by HCD (step 385), mass analysis, by a mass analyzer, of the ions remaining after the fragmentation step, thereby generating a mass spectrum of fragments (step 387), determination if all m/z ranges have been interrogated (step 391) and, if more m/z ranges are to be interrogated, changing or incrementing the m/z range to be next interrogated. Optionally, an attempt may be made (step 389a) to identify compounds that correspond to lines that occur within the respective interrogated m/z range during each iteration of the loop of steps 381 through 393, but these attempts may optionally be performed outside of the loop (step 389b). The compound identification step (step 389a or 389b) may make use of the observed mass spectral positions of lines determined during the mass analysis (or analyses) of fragment ions (step 387) and possibly the mass spectral positions, as may be observed in step 384, of ions from which the fragments were formed by HCD.

Because the method 370 pertains to data-independent analysis, the positions of the various interrogated m/z ranges are, in general, not determined by the results of the high-resolution MS survey scan (step 379) but are instead, all or mostly pre-determined, proceeding in incremental steps from a lowermost m/z range to an uppermost m/z range (or vice versa) in predetermined increments. The incremental spacing between successive m/z ranges may be constant or, alternatively, may vary during the course of an analysis. Adjacent interrogated m/z ranges (m/z windows) may be contiguous and may overlap one another. Less preferably, there are gaps between some of the interrogated m/z ranges. One situation in which gaps may beneficially occur between interrogated m/z ranges is when certain m/z ranges are skipped based on information from the high-resolution MS survey scan (step 379) that no peaks are present in such skipped regions.

A mass isolation (step 381) is performed during each iteration of the loop of steps 381 through 393, corresponding to a respective interrogated m/z range. Since the identities of compounds in the sample are not generally known beforehand, the width of the isolation window will generally be chosen to be sufficiently large such that at least one mass spectral line of a compound of potential diagnostic interest is likely to be present within the isolation window. Thus, the isolation window width used in step 381 will, in general, be greater than window widths usually employed (approximately 2 Th) when the positions of lines are known (as in a data-dependent experiment) or expected (as in a targeted experiment). An optimal isolation window width may be pre-chosen based on routine experimentation of similar or identical samples. The optimal window width may be entered, as a parameter, during an additional input step at the commencement of execution of the method 370. If no optimal window width is available, then a default window width, such as a window width within the range 4-6 Th, inclusive, may be employed.

Similarly, a PTR step (step 383) is performed during each iteration of the loop of steps 381 through 393. The PTR step is performed under the application of a supplemental ion-parking AC waveform to electrodes of an ion trap within which the PTR reaction occurs. The frequency of the waveform corresponds to a particular m/z value, $(m/z)_{park}$. Any PTR product ions that are formed during the course of the reaction and that coincidentally comprise an m/z value that is very nearly equal to $(m/z)_{park}$ will be inhibited from participating in any further charge-reducing reactions with PTR reagent ions. Accordingly, such ion species will accumulate at $(m/z)_{park}$ while all other ions will continue to have their charges reduced or neutralized. If $(m/z)_{bound}$ is the lowermost boundary of an isolation window, then the only compounds for which mass spectral lines will be parked during step 383 will be those compounds for which the spacing, $\Delta(m/z)$, between adjacent charge states (of ions comprising multi-protonated versions of the compounds) is such that $\Delta(m/z) \leq [(m/z)_{park} - (m/z)_{bound}]$. Since the identities of compounds in the sample are not generally known beforehand, it is generally unknown how many compounds will have their spectral signatures "parked" at $(m/z)_{park}$. In general, only a few compounds, at most, will be expected to fulfill the above condition. However, the number of compounds, if any, for which this condition is fulfilled will increase with an increase in spacing between $(m/z)_{park}$ and $(m/z)_{bound}$. To some extent, a desired spacing, $\Delta(m/z)_{desired}$, between adjacent charge states may be estimated based on an estimated or known molecular weight range of compounds of potential diagnostic interest. In such situations, the supplemental waveform may be chosen such that the quantity $[(m/z)_{park} - (m/z)_{bound}]$ is just slightly greater than $\Delta(m/z)_{desired}$.

Figure 3D:
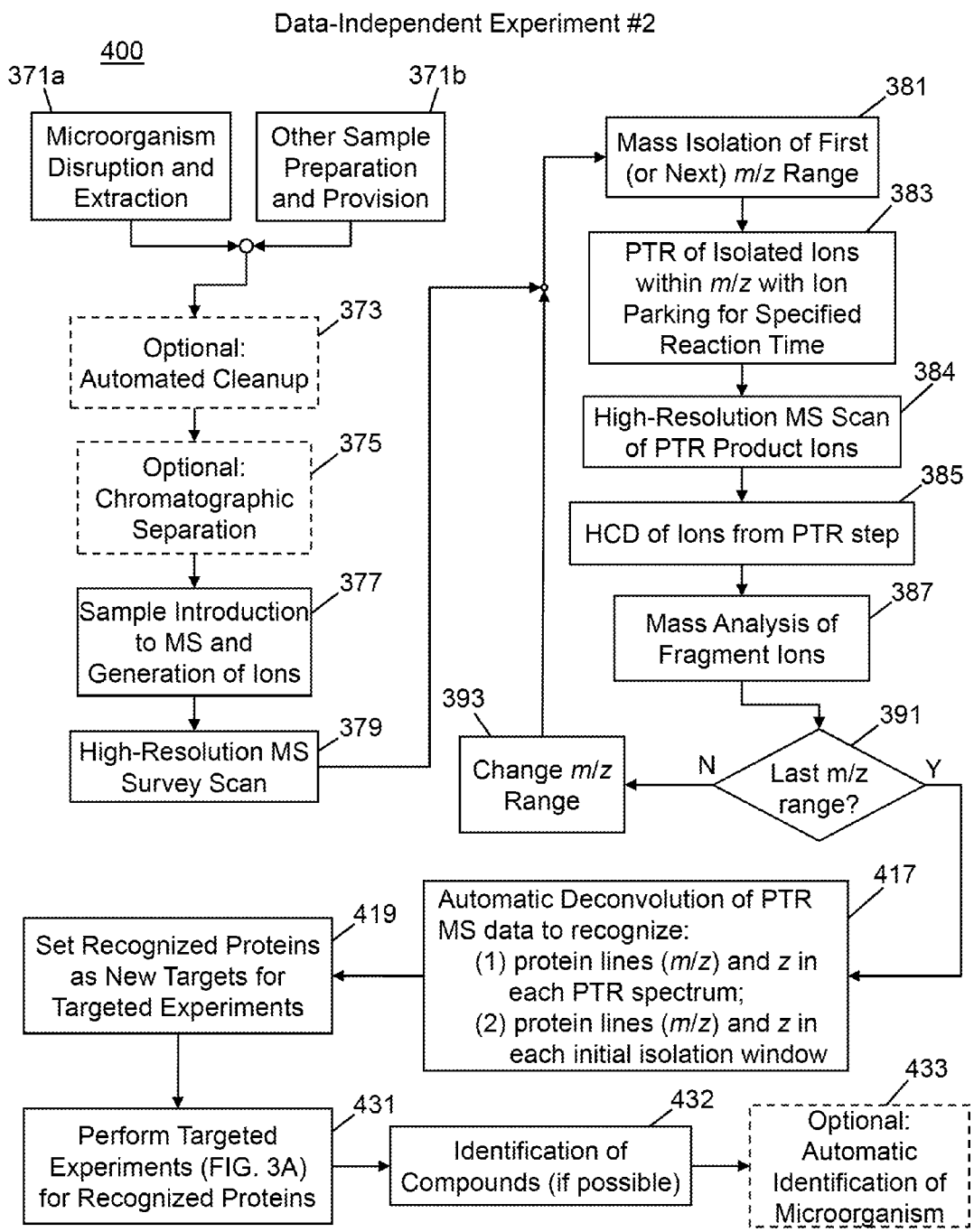
FIG. 3D is a schematic flow chart of a fourth exemplary method in accordance with the present teachings, said fourth method directed towards data-independent determination of the presence and/or concentration of one or more proteins in a sample.

FIG. 3D is a schematic flow chart of a fourth exemplary method in accordance with the present teachings. The method 400 illustrated in FIG. 3D is an alternative data-independent method for determining of the presence and/or concentration of one or more proteins in a sample. Many steps of the method 400 (FIG. 3D) are similar to corresponding steps in the method 370 (FIG. 3C). Accordingly, these corresponding steps are similarly numbered in FIGS. 3C-3D. Specifically, the steps (371a or 371b) through step 393 of the method 400 are similar to and are organized similarly to the corresponding steps of the method 370, except that the mass analysis of PTR product ions (step 384) is no longer optional and is a high-resolution mass analysis in method 400.

Similarly to the already described method 300, the method 400 includes a set of steps (specifically, steps 381-393) that are executed repeatedly, where each execution of the set of steps corresponds to interrogation of a different respective m/z range. The main difference between method 370 and method 400 occurs in the steps that are executed after the final m/z range has been interrogated. In the method 400, once the last m/z range has been interrogated (determined in step 391), the "Y" (yes) branch of step 391 diverts execution to new step 417 at which an automatic mathematical deconvolution of each obtained high-resolution PTR MS scan (from step 384) is performed so as to recognize, for each such scan: (1) protein lines, m/z, and charge states, z, in each PTR spectrum; and (2) protein lines, m/z, and charge states, z, in each initial isolation window. A suitable automated real-time mass spectral deconvolution technique has been described in the aforementioned co-pending and commonly assigned U.S. Provisional Application No. 62/132,124 filed on Mar. 12, 2015 in the names of inventors Yip et al. and titled "Methods for Data-Dependent Mass Spectrometry of Mixed Biomolecular Analytes". In the subsequent step 419, the recognized protein lines and charge states as determined by the mathematical deconvolution are set as input for execution of one or more targeted experiments (e.g., method 300) and the various targeted experiments are then performed (step 431). Using the data obtained in the subsequent targeted experiments, possibly supplemented by data obtained in steps 384 and 387 of the method 400, an attempt may be made to identify compounds in the sample (step 432). Using a sufficient number of identified compounds, an identification of a micro-organism from which the sample was derived may be made (step 433), if appropriate.

EXAMPLES

Example 1. Mass Spectral Analysis of Ubiquitin Mixture

Figure 4C:
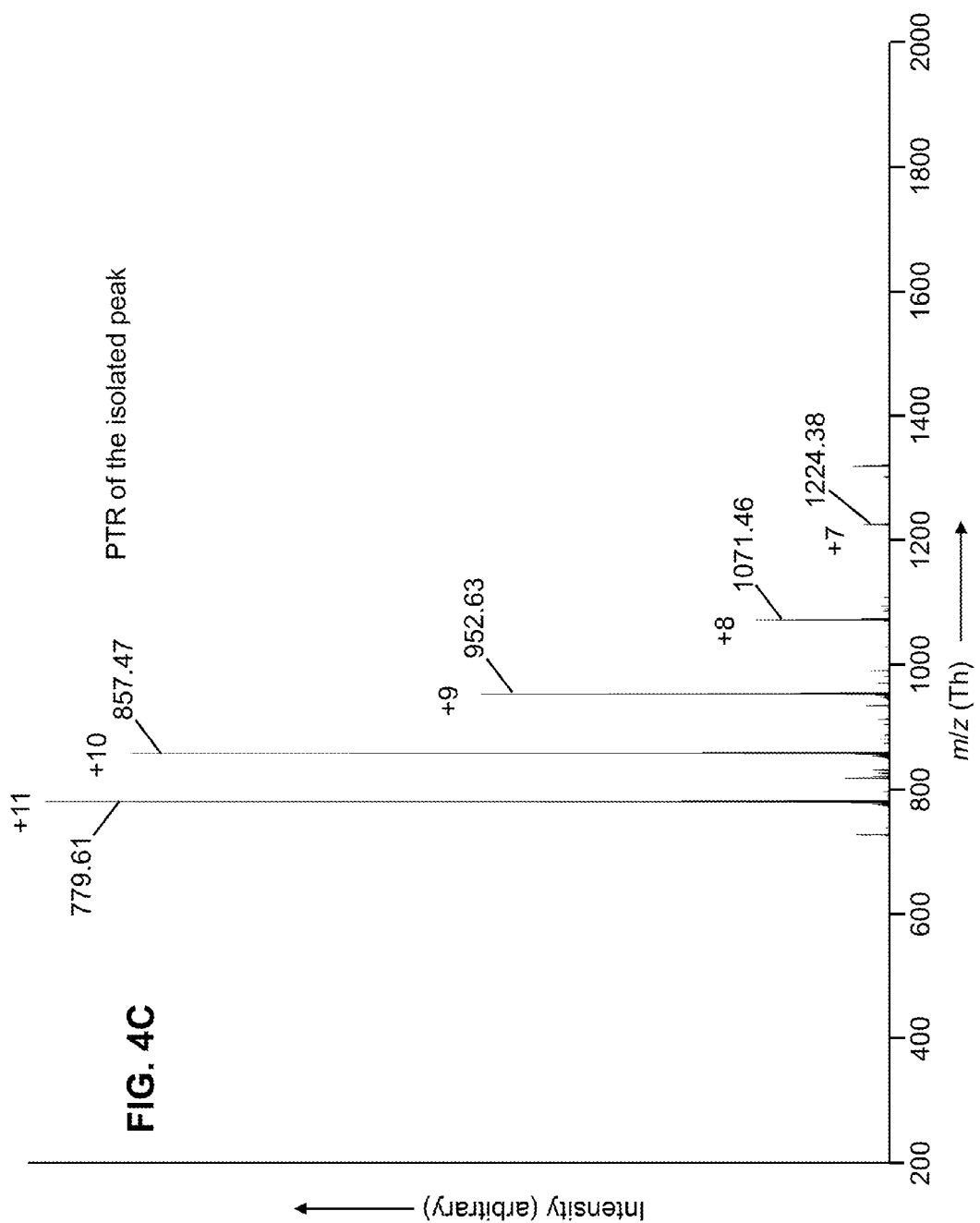
FIG. 4C is a mass spectrum of ions comprising a plurality of multiply protonated ubiquitin molecules having charge states of +11 or less generated by reaction of the isolated population depicted in FIG. 4B with PTR reagent ions for 50 milliseconds.

FIGS. 4A, 4B, 4C and 4D illustrate application of the combined techniques of PTR and HCD to analysis of a solution of ubiquitin containing abundant polymeric contaminants. FIG. 4A is a graphic depiction of a survey scan ($MS^1$ scan) of the sample. Peaks which may be recognized as relating to the ubiquitin compound are labeled with their charge states and m/z positions. Most or all of the remaining peaks, a few select ones of which are labeled with their m/z positions, correspond to polymeric contaminants. In order to simplify the spectrum, a sub-population of ions within an isolation window of width 2 Th around the expected position of the ubiquitin +13-charge-state peak were isolated (mass spectrum of isolate shown in FIG. 4B) and the isolated original ions were exposed to PTR reagent, without ion parking, for 50 ms. A mass spectrum of the first-generation product ions produced by this PTR step is illustrated in FIG. 4C. After the PTR step, several well-resolved ubiquitin lines, indicated by their charge states and m/z positions, are observed. As expected, the highest charge state of the ubiquitin ion (+12 and greater) that were previously present are completely eliminated by reaction with the PTR reagent; thus, the overall distribution is shifted to lower charge states. Although the ubiquitin lines in FIG. 4C are well exposed, the weak background lines indicate that a small proportion of contaminant ions were co-isolated along with ubiquitin +13 ion in the original isolation step.

Figure 4D:
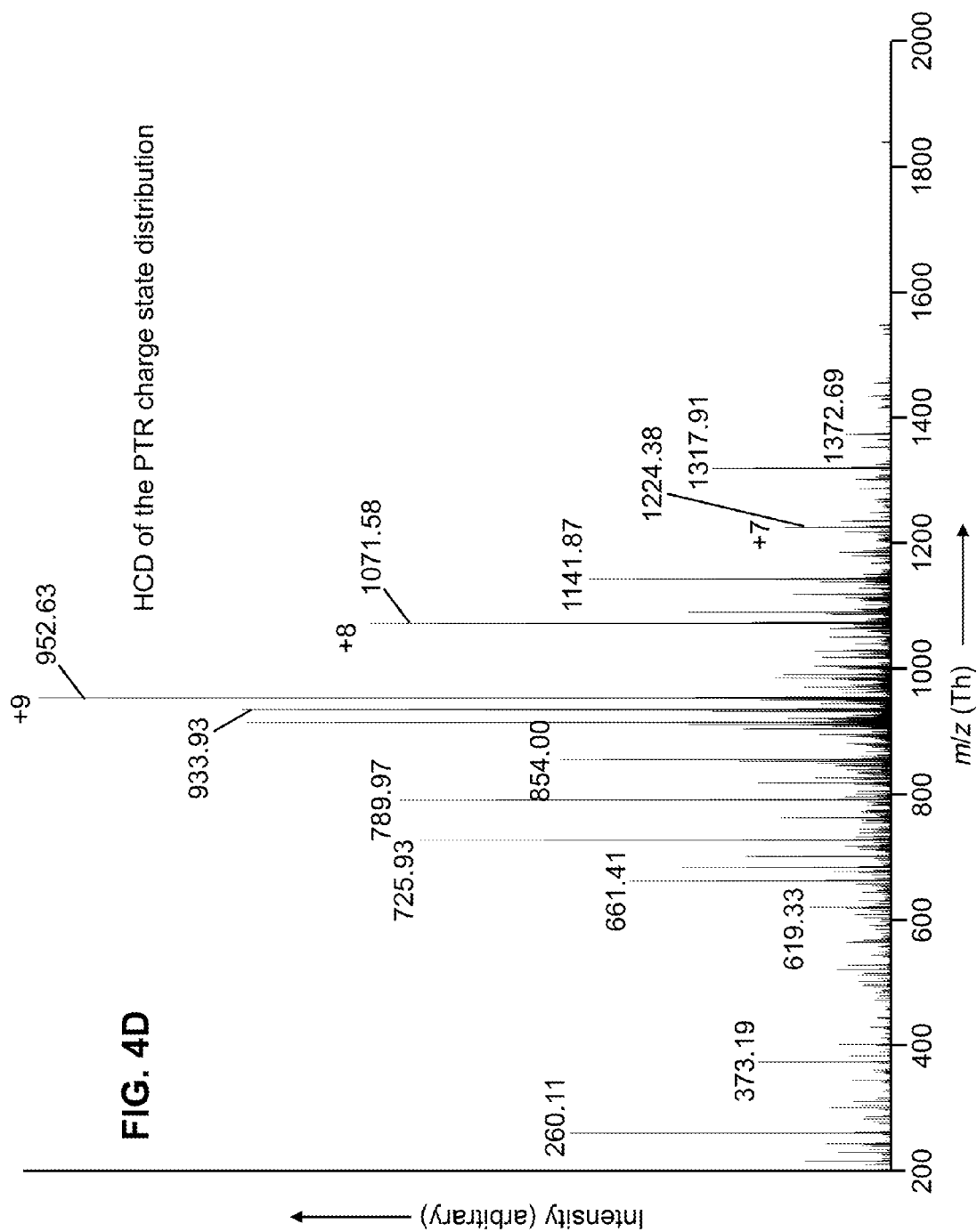
FIG. 4D is a mass spectrum of fragment ions generated from the population of ions depicted in FIG. 4C by the technique of higher-energy collisional dissociation using a normalized collision energy value of 20.

The population of first-generation product ions illustrated in FIG. 4C were subjected to a fragmentation step according to the technique of Higher collisional Energy Dissociation (HCD). A mass spectrum of the resulting fragments and residual unfragmented ions was obtained, as shown in FIG. 4D. It is known that the kinetic energy imparted to ions during the HCD procedure is dependent upon the initial charge state of the ions. When a set of ions of differing charge states, such as those shown in FIG. 4C, are simultaneously accelerated into a collision gas, the collision energy may be adjusted such that only ions with charge states greater than a certain value are caused to fragment. In the present instance, a collision voltage in accordance with a normalized collision energy (NCE) value of 20 was applied. Comparison of FIG. 4D with FIG. 4C shows that, whereas the ubiquitin ions having the +10 and +11 charge states are completely fragmented, the ions having charge states +9, +8 and +7 retain essentially the same relative proportions as in the pre-fragmentation spectrum, indicating little or no fragmentation of these ions. Thus, the results indicate that the applied normalized collision energy is insufficient, in this case, to cause fragmentation of ions having a charge state of less than approximately +8. Control of the normalized collision energy in this fashion provides a check against over-fragmentation.

Example 2. Mass Spectral Analysis of Two-Protein Mixture

Figure 5A:
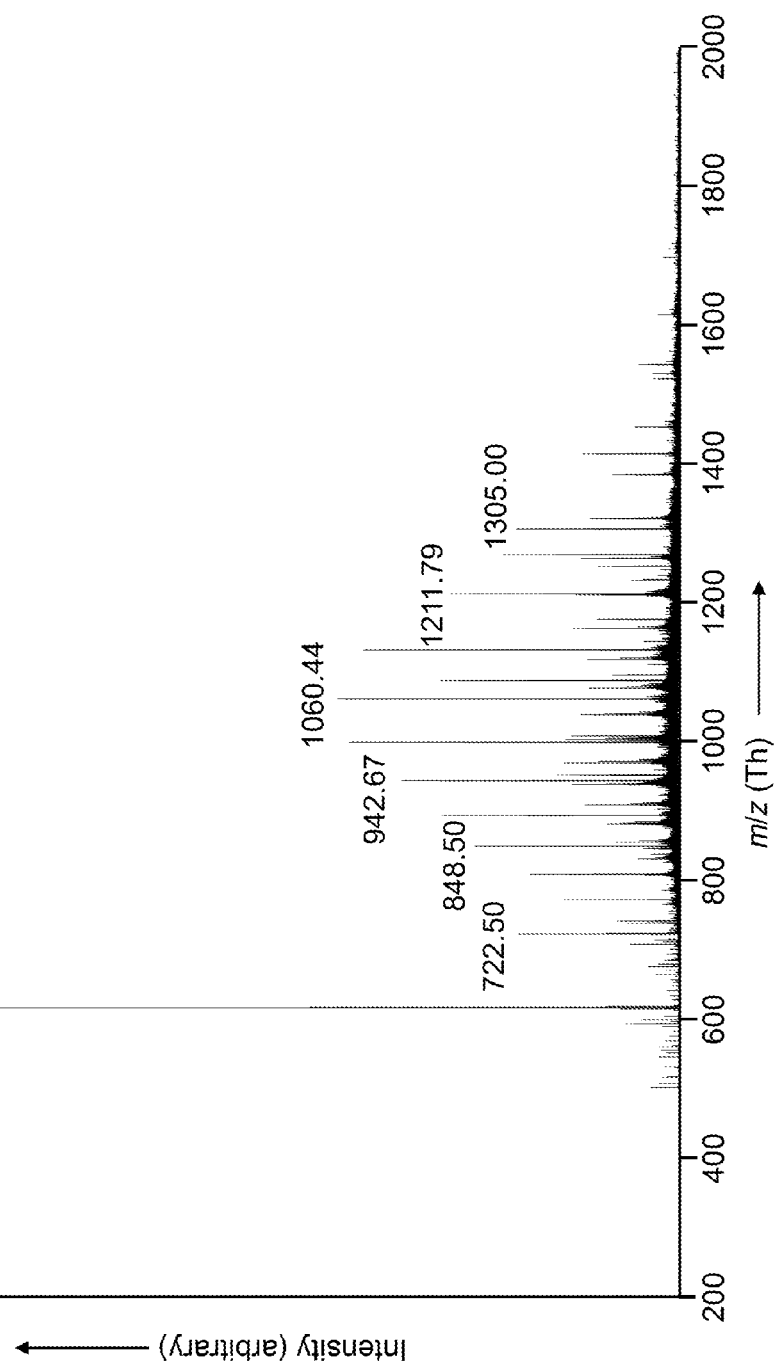
FIG. 5A is a mass spectrum of ions derived from a solution containing a mixture of carbonic anhydrase and myoglobin also showing ions of a heme unit produced during sample preparation.
Figure 5C:
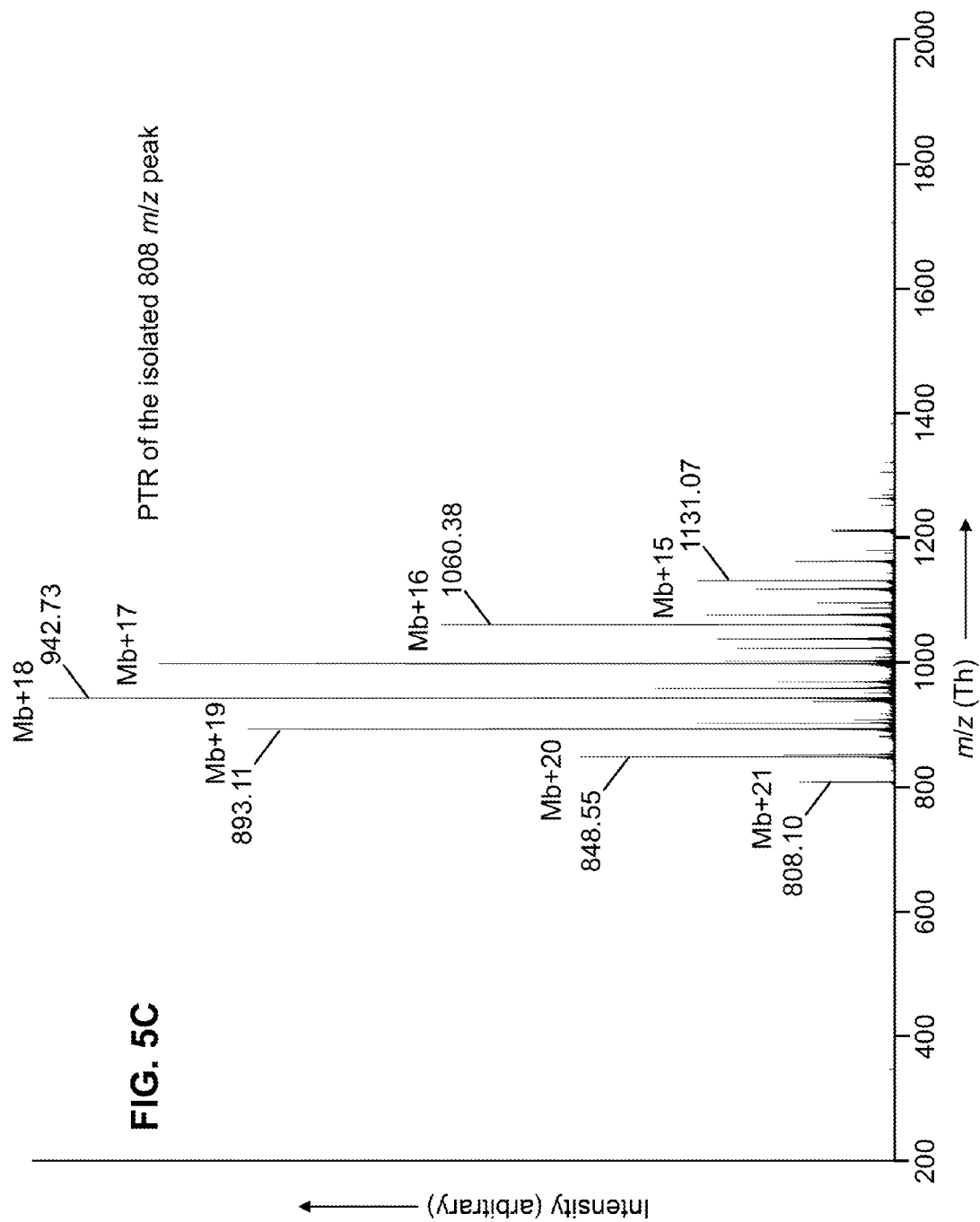
FIG. 5C is an illustrative mass spectrum of ions generated by reaction of the isolated ion population depicted in FIG. 5B with PTR reagent ions for 30 milliseconds, exhibiting the phenomenon of potential signal enhancement (co-isolation) of multiple species in an initial PTR stage without ion parking.

FIGS. 5A, 5B, 5C, 5D, 5E and 5F illustrate application of the combined techniques of PTR and HCD to analysis of a mixture of carbonic anhydrase and myoglobin. FIG. 5A is an $MS^1$ survey spectrum of the mixture of carbonic anhydrase and myoglobin in solution. The tall peak at 616 Th is the signature of the heme moiety that is otherwise non-covalently attached to myoglobin. The sample preparation results in separation of the heme (holo-myoglobin becoming apo-myoglobin). The heme peak is commonly observed. In order to simplify the spectrum, a sub-population of ions within an isolation window of width 2 Th around the expected position of the myoglobin +21-charge-state peak were isolated (mass spectrum of isolate shown in FIG. 5B) and the isolated original ions were exposed to PTR reagent, without ion parking, for 30 ms. A mass spectrum of the first-generation product ions produced by this PTR step is illustrated in FIG. 5C. The general form of the mass spectrum illustrated in FIG. 5C indicates the presence of three different protein charge state distributions (myoglobin, carbonic anhydrase and one other) of which only the myoglobin peaks are labeled.

Figure 5D:
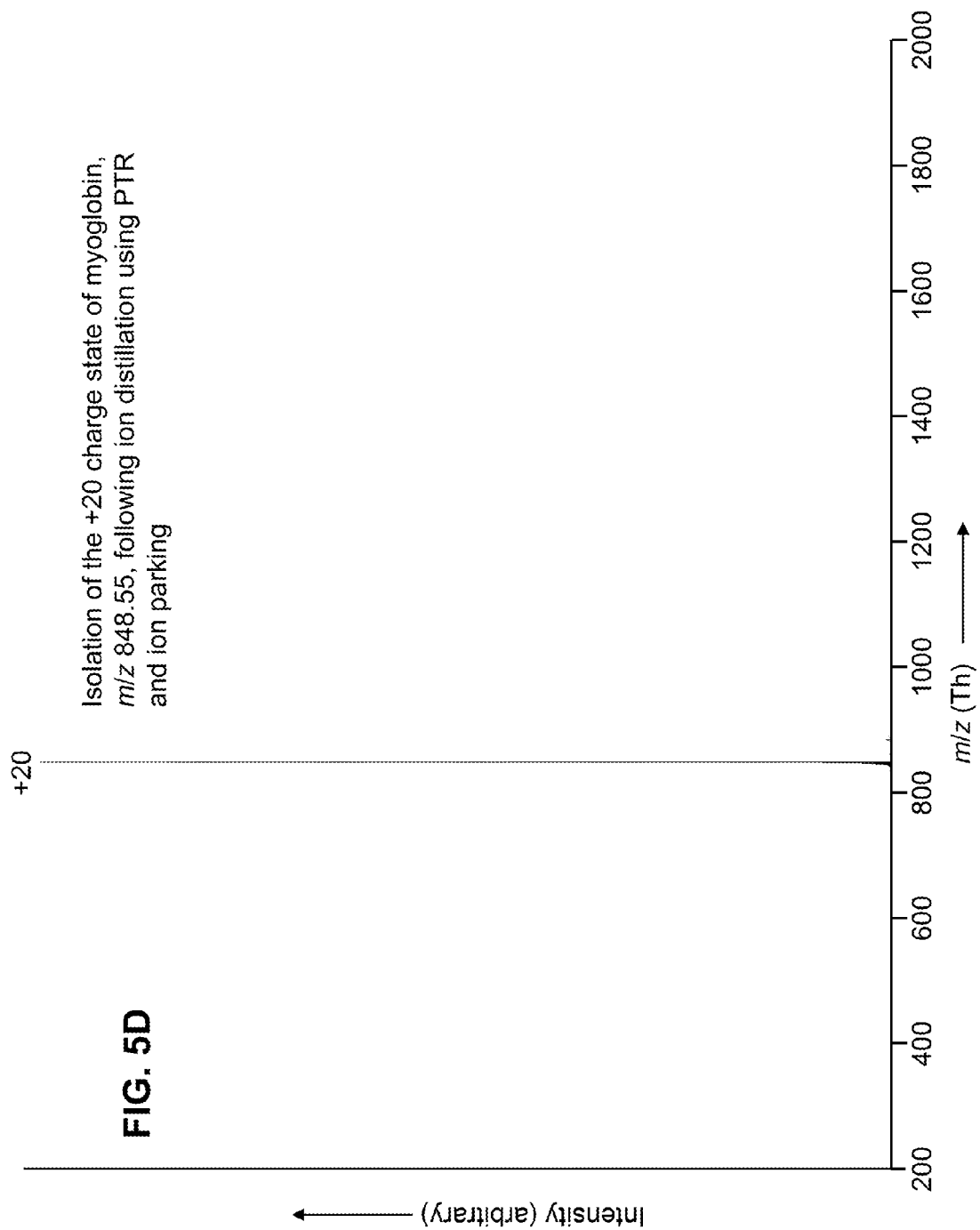
FIG. 5D is a mass spectrum of ions consisting essentially of purified multiply protonated myoglobin molecules having charge state +20 generated by reaction of the isolated ion population depicted in FIG. 5B with PTR reagent ions for 30 milliseconds during application of ion parking, followed by isolation of the PTR product ions at approximately 808 Th, showing efficient concentration and isolation of the myoglobin mass spectral signature.
Figure 5E:
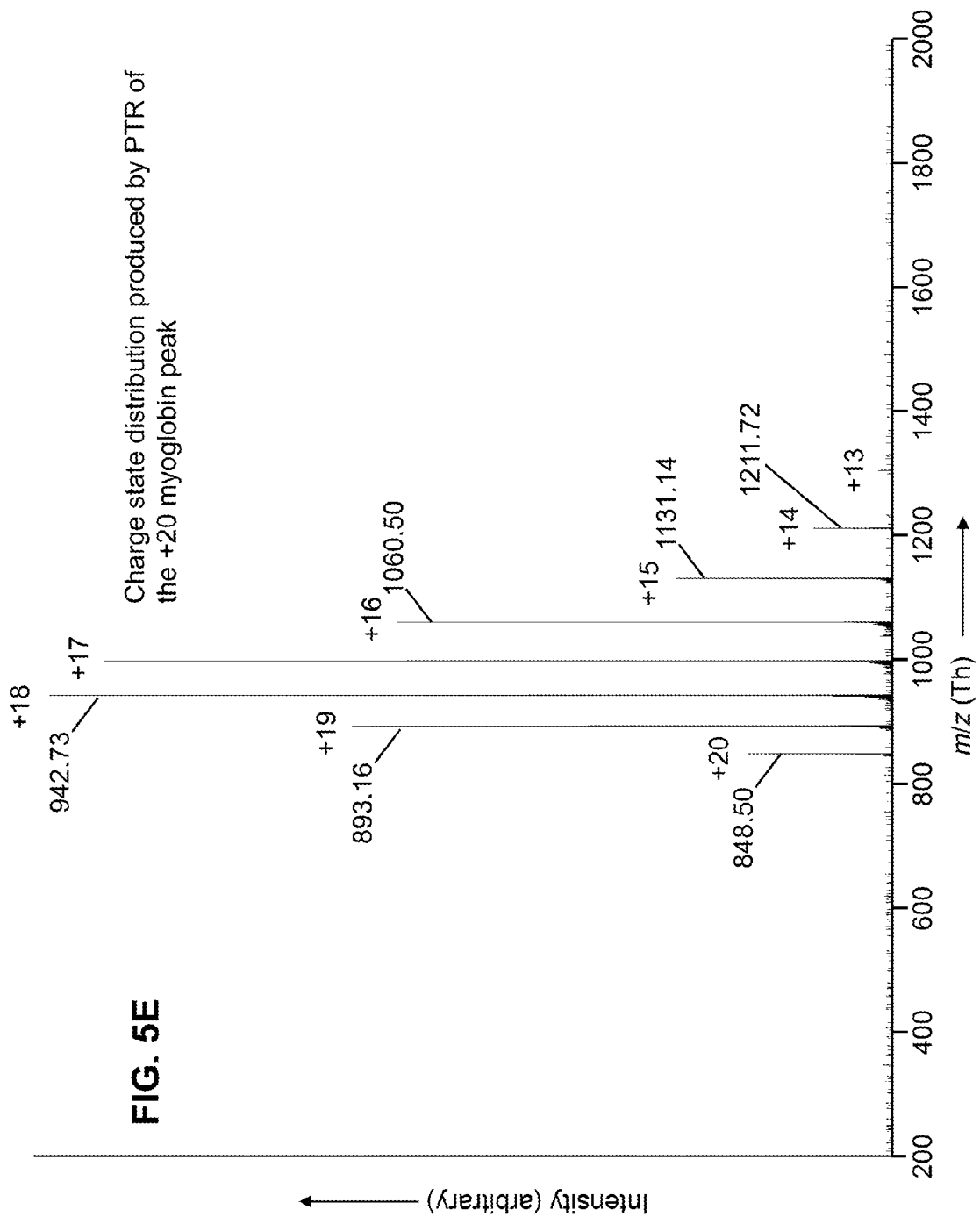
FIG. 5E is a mass spectrum of a population of ions generated by still further reaction of the purified multiply protonated myoglobin molecules of charge state +20, as depicted in FIG. 5D, with PTR reagent for 2 milliseconds so as to produce multiply protonated myoglobin molecules having a range of charge states.

FIG. 5D is a mass spectrum of ions generated by PTR and ion parking of the +21 charge state of myoglobin from the ion population shown in FIG. 5B with PTR reagent ions for 30 milliseconds using a waveform chosen to prevent PTR charge reduction at the m/z position of +20 peak of myoglobin at 848.55 Th (formed during the PTR step from the +21 peak at 808.10 Th) followed by isolation of the +20 ions. The ions resulting from these steps essentially consist of the pure ion species of myoglobin in the +20 charge state. This isolated ion species were then subjected to a second PTR step so as to produce a charge state distribution, the mass spectrum of which is shown in FIG. 5E.

Figure 5F:
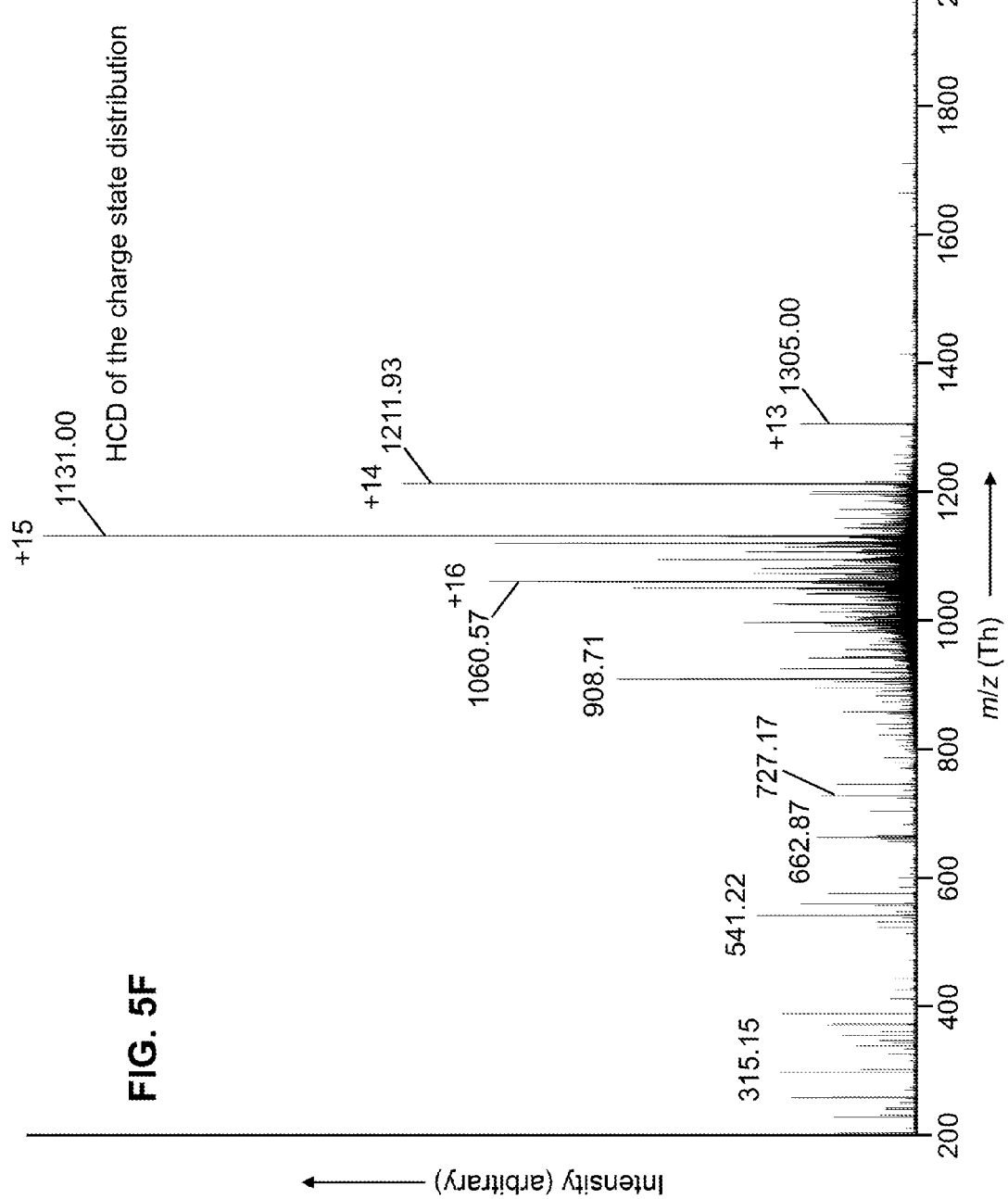
FIG. 5F is a mass spectrum of fragment ions generated from the population of ions depicted in FIG. 5E by the technique of higher-energy collisional dissociation.

The ions of the myoglobin charge state distribution (FIG. 5E) where subjected to an HCD fragmentation step. A mass spectrum of the resulting fragments and residual unfragmented ions was obtained, as shown in FIG. 5F. The mass spectrum of FIG. 5F shows that an abundance of fragments were formed by nearly complete fragmentation of ions of the +17 through +20 charge states as well as a substantial portion of the ions of the +16 charge state but that the myoglobin ions of charge states +15 and below remain substantially unfragmented. The set of fragments depicted in FIG. 5F were analyzed by ProSight software, available from Northwestern University to reconstruct the sequence of myoglobin. It was found that the procedure described above (multiple PTR steps followed by HCD fragmentation) produced a total of 31 recognizable ions (30 y-ions and 1 b-ion) which were sufficient to unambiguously reconstruct the myoglobin sequence. These results were superior to results obtained when only a single PTR step, followed by fragmentation, was employed. In this latter case, only 23 total ions were recognized. Application of HCD by itself, without a prior PTR purification step produced even worse results, with only five total fragment ions being recognized.

Example 3. Mass Spectral Analysis of Myoglobin in Bacterial Lysate

Figure 6A:
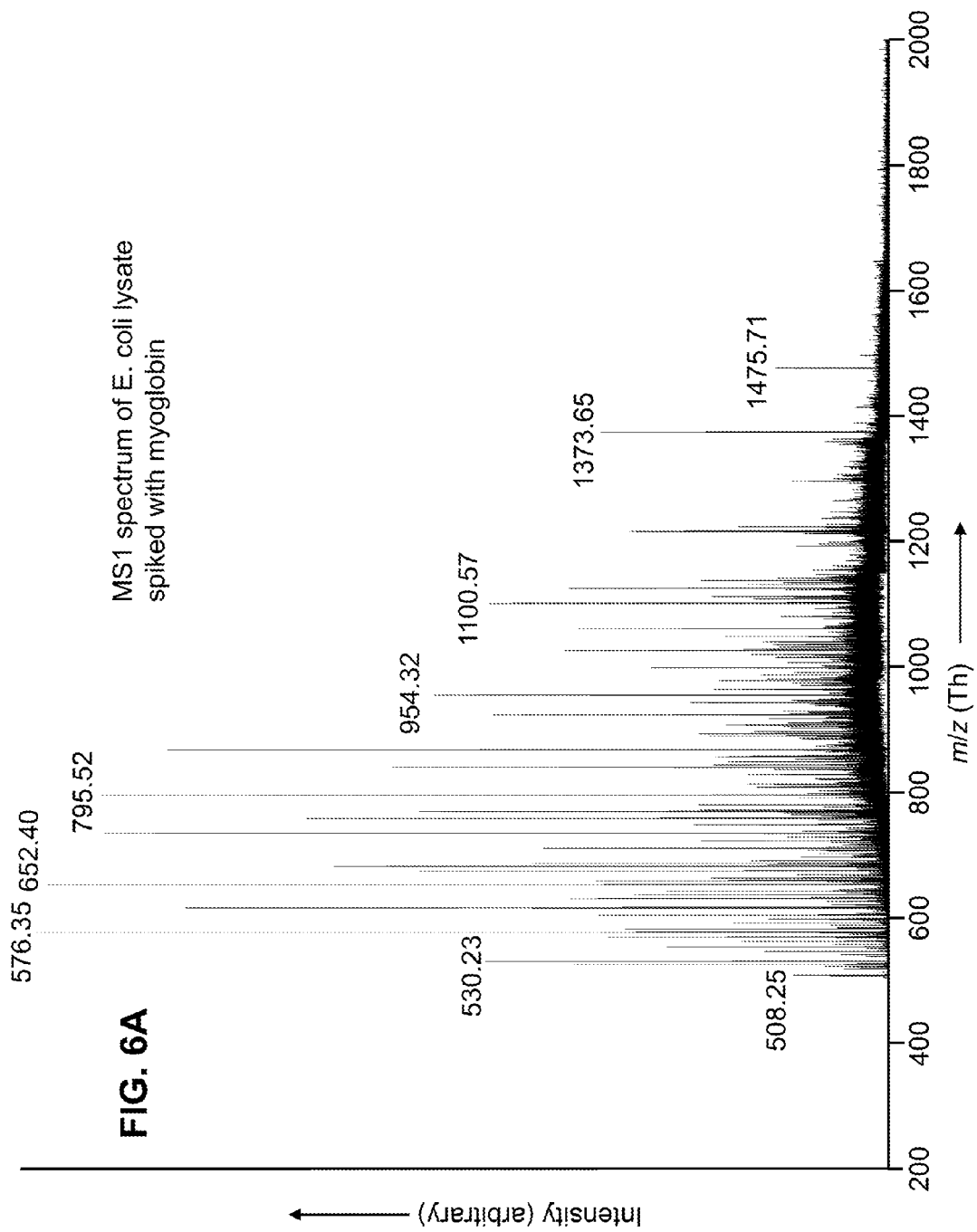
FIG. 6A is a mass spectrum of ions generated from a lysate of the bacterium *E. Coli* containing added myoglobin.
Figure 6B:
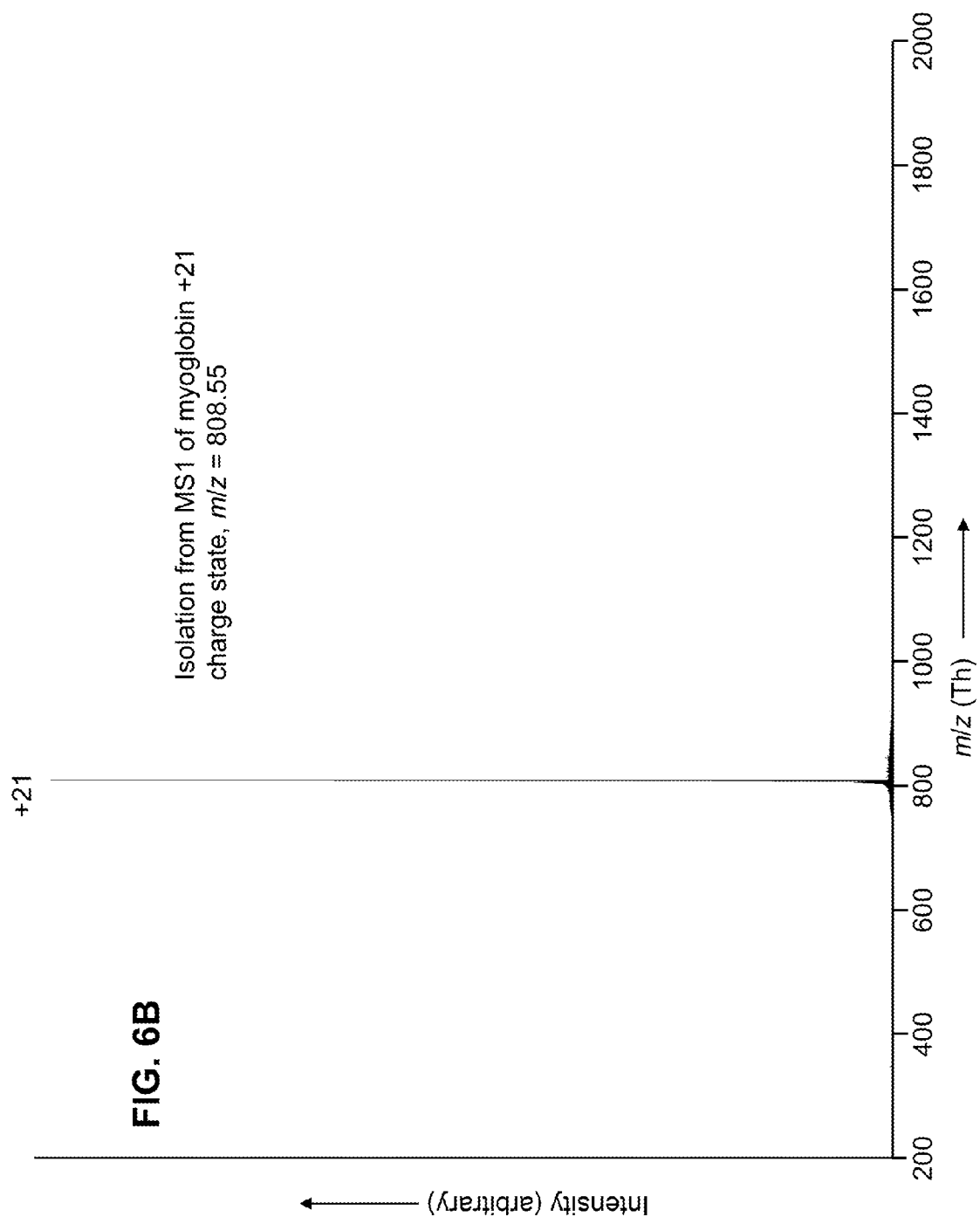
FIG. 6B is a mass spectrum of ions remaining after m/z isolation of the ion population depicted in FIG. 6A within a 2 Th-wide isolation window around 808 m/z, said isolation window encompassing multiply-protonated myoglobin ions having charge state +21.

FIGS. 6A, 6B, 6C, 6D, 6E, 6F and 6G illustrate application of the combined techniques of PTR and HCD to analysis of myoglobin within a bacterial lysate. The sample was prepared by adding a small amount of myoglobin into a lysate of the bacterium *E. coli*. FIG. 6A shows an $MS^1$ survey scan of the sample. Peaks attributable to myoglobin (not labeled) in the mass spectrum of FIG. 6A are nearly invisible in the midst of many peaks attributable to bacterium-derived compounds. During mass spectral analysis of this sample, a sub-population of the original ions were isolated within an isolation window of width 2 Th centered at an m/z value of 808 Th, which is the expected position of the ion species comprising the multi-protonated myoglobin molecule of charge state +21. FIG. 6B shows a mass spectrum of the isolated ions.

Figure 6C:
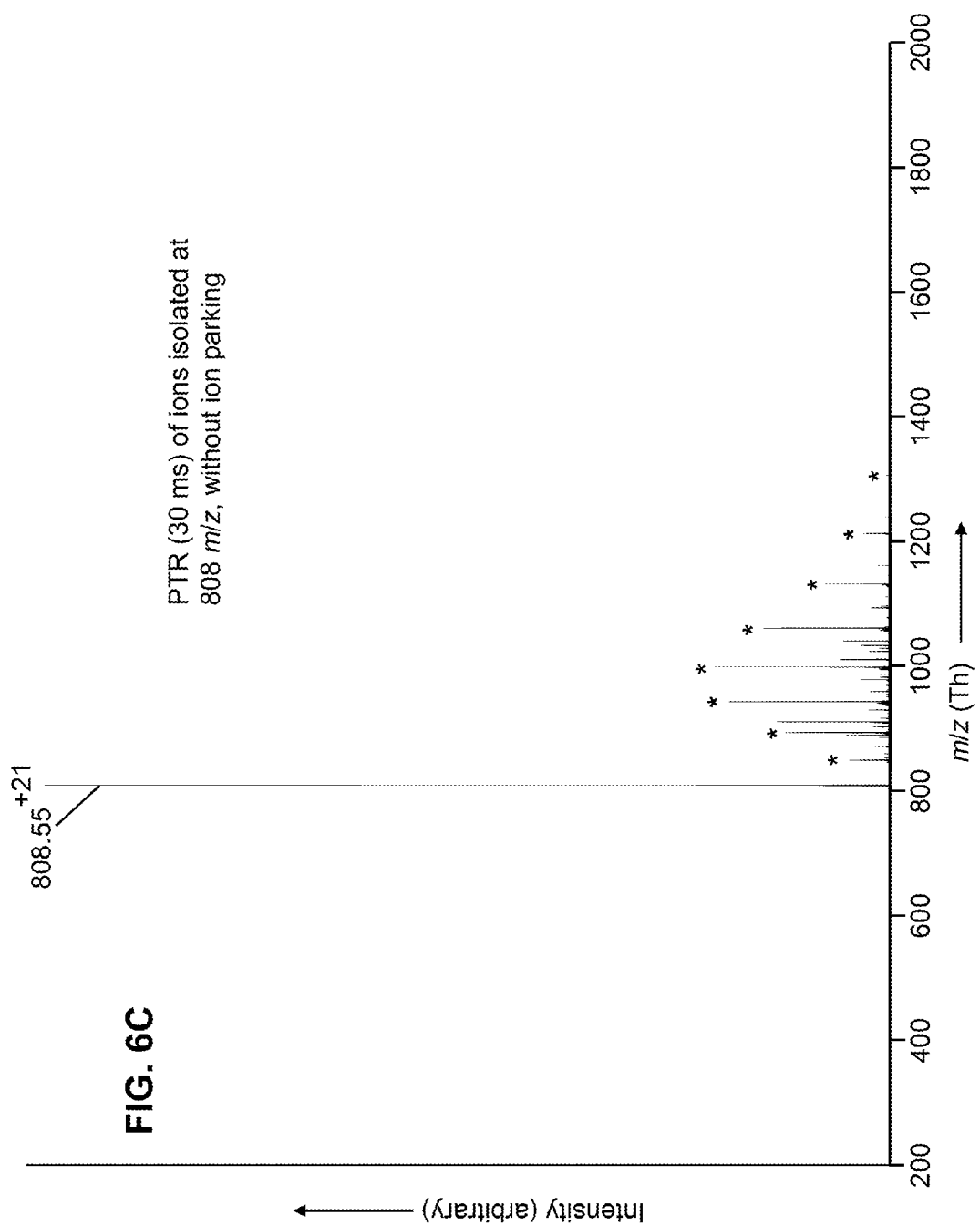
FIG. 6C is an illustrative mass spectrum of ions generated by reaction of the isolated ion population depicted in FIG. 6B with PTR reagent ions for 30 milliseconds without application of ion parking, exhibiting the phenomenon of potential signal enhancement (co-isolation) of multiple species in an initial PTR stage without ion parking.
Figure 6D:
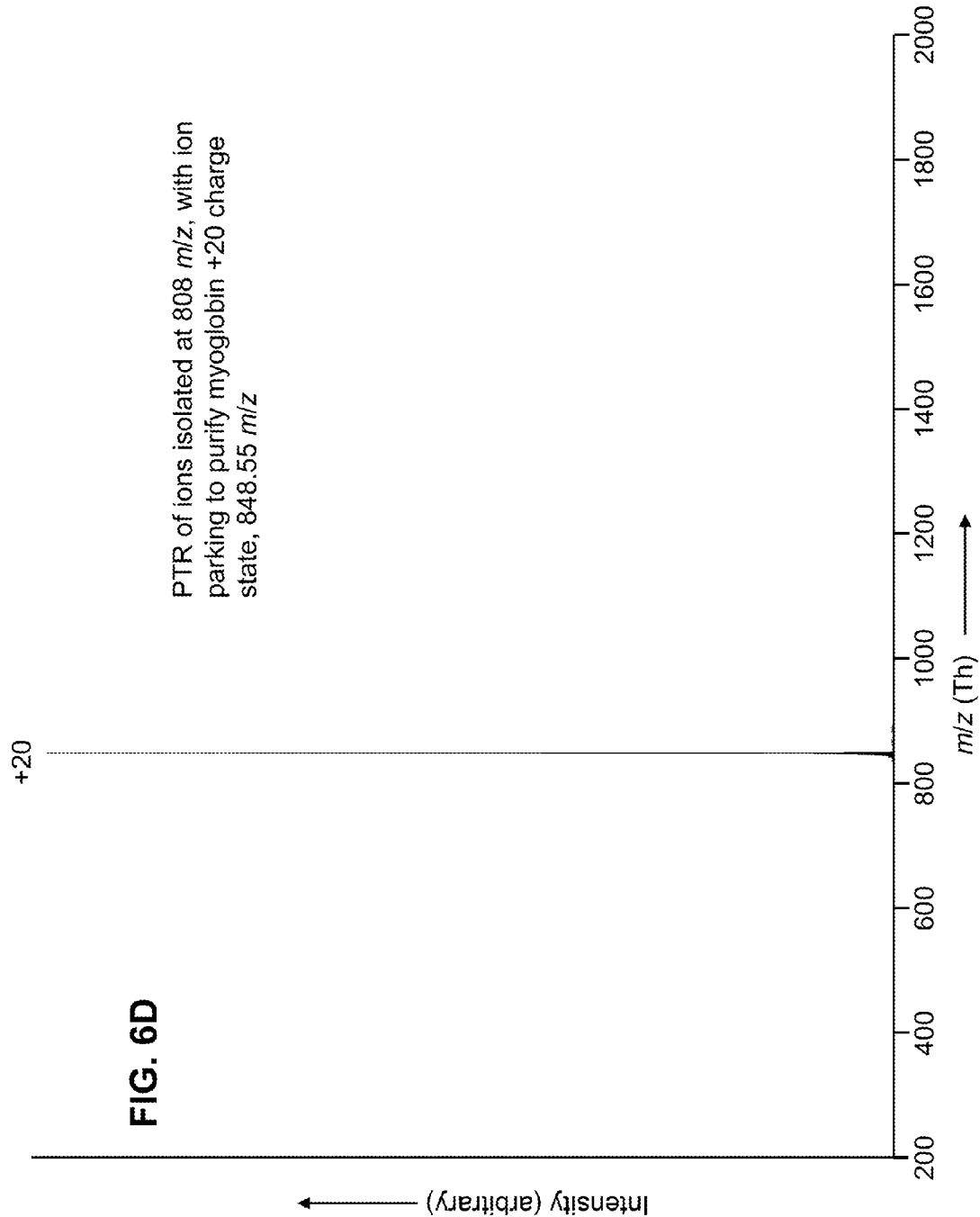
FIG. 6D is a mass spectrum of ions consisting essentially of purified multiply protonated myoglobin molecules having charge state +20 generated by reaction of the isolated ion population depicted in FIG. 6B with PTR reagent ions for 30 milliseconds during application of ion parking, followed by mass isolation.
Figure 6F:
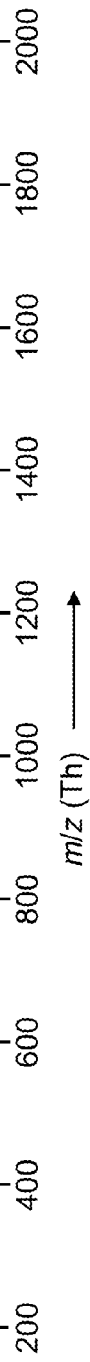
FIG. 6F is a mass spectrum of fragment ions generated from the ion population depicted in FIG. 6E by the technique of higher-energy collisional dissociation using a normalized collision energy value of 20.
Figure 6G:
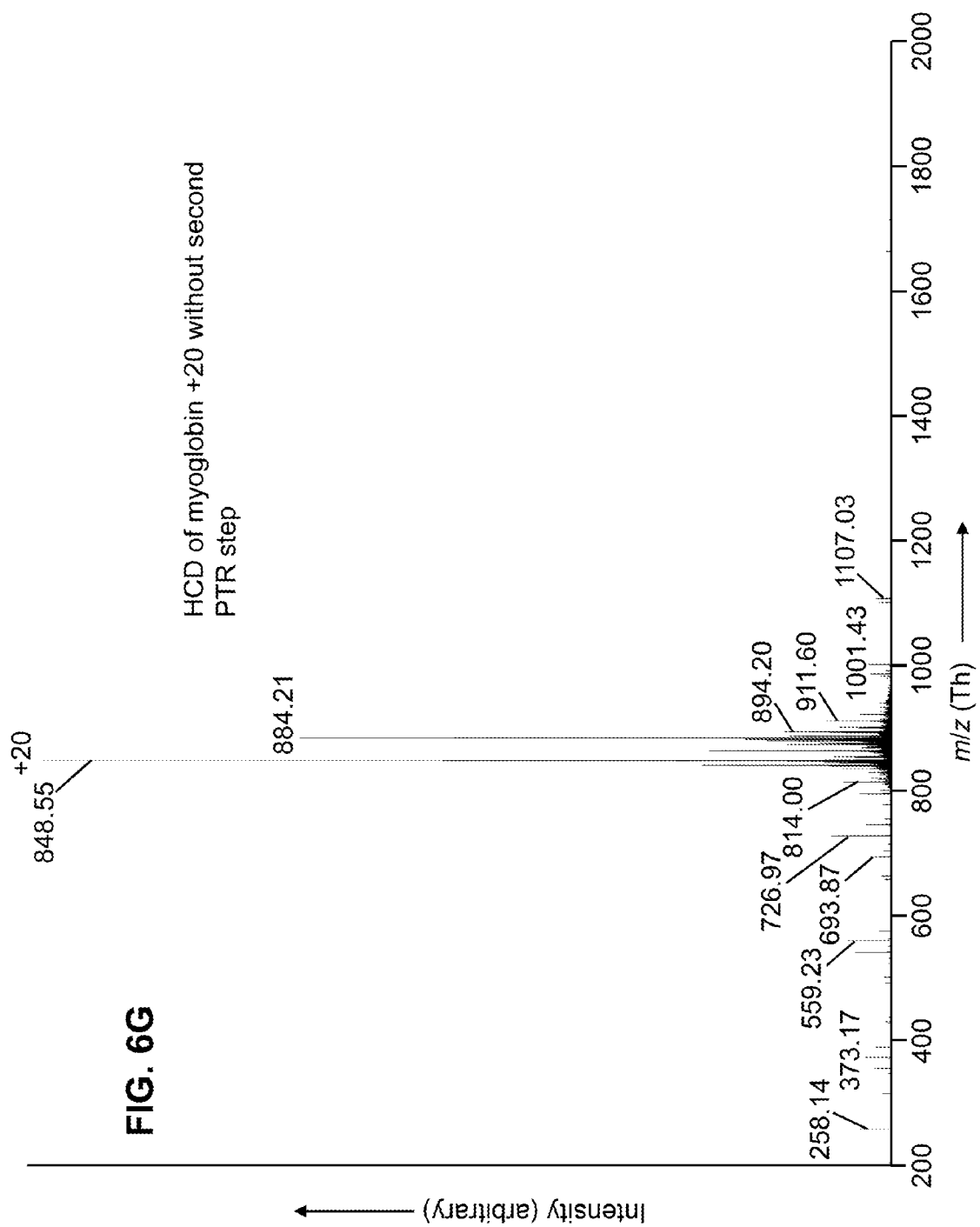
FIG. 6G is a mass spectrum of fragment ions generated from the ion population depicted in FIG. 6D by the technique of higher-energy collisional dissociation.

FIG. 6C illustrates a test mass spectrum that was obtained after reacting a portion of the isolated ions depicted FIG. 6B with PTR reagent for 30 ms in the absence of ion parking. Under these reaction conditions, only a small portion of the myoglobin species of charge state +21 is reacted so as to generate reduced-charge-state myoglobin species (indicated by asterisks in FIG. 6C) having charge states +20, +19, +18, +17, +16, +15, +14, +13 and possibly others. The presence of additional lines in the mass spectrum of FIG. 6C indicates ions of other compounds were co-isolated together with the myoglobin during the original isolation step. Therefore, in order to eliminate the contaminant species, the ion population depicted in FIG. 6B was reacted with PTR reagent for 50 ms under the application of an ion parking waveform so as to stop the reduction of myoglobin ions at the +20 charge state (848.55 Th). The ion species at this m/z value was then isolated, thus yielding an essentially pure myoglobin species as depicted in FIG. 6D.

Subsequent to its isolation, the purified myoglobin ion species of the +20 charge state (FIG. 6D) was further reacted with PTR reagent for 1 ms in the absence of ion parking so as to create a distribution of charge states as depicted in FIG. 6E. This set of charged myoglobin ion species was then fragmented by HCD using a normalized collision energy value of 20 so as to generate the fragment spectrum depicted in FIG. 6F. In addition to fragments, the mass spectrum of FIG. 6F also exhibits peaks attributable to unfragmented intact myoglobin ions. For comparison, FIG. 6G exhibits a fragment-ion spectrum generated by HCD fragmentation of the +20 charge state of myoglobin in the absence of a second PTR purification step.

The discussion included in this application is intended to serve as a basic description. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. Any patents, patent applications, patent application publications or other literature mentioned herein are hereby incorporated by reference herein in their respective entirety as if fully set forth herein, except that, in the event of any conflict between the incorporated reference and the present specification, the language of the present specification will control.

What is claimed is:

1. A method for identifying the presence or absence of a protein or polypeptide analyte compound within a liquid sample comprising a mixture of compounds that includes a plurality of protein compounds or a plurality of polypeptide compounds or pluralities of both protein and polypeptide compounds, the method comprising:
   (a) receiving, from a user or a data file, a value of a mass-to-charge ratio $(m/z)_p$ and a charge state, $z_p$, of an ion comprising a molecule of the protein or polypeptide analyte compound having $z_p$ adducted protons;
   (b) forming positively charged ions of the mixture of compounds of the portion of the liquid sample by electrospray ionization in an ion source of a mass spectrometer, the positively charged ions comprising a plurality of ion species;
   (c) isolating a subset of the ion species comprising an m/z range that includes the received m/z value;
   (d) generating a plurality of first-generation product ion species from the isolated first subset of ion species by causing the isolated first subset of ion species to be reacted, in an ion trap, with anions of a reagent compound that, upon reaction, extract protons from each of one or more ion species that comprises a protonated molecular species of a protein or polypeptide compound, the reaction performed for a predetermined time duration during which a first supplemental oscillatory voltage waveform is applied to electrodes of the ion trap, said waveform including a frequency that matches a frequency of motion of ions having a second m/z that corresponds to a the molecule of the analyte compound having $(z_p-n)$ adducted protons, where $1 \le n < z_p$;
   (e) isolating a subset of the first-generation product ion species comprising another m/z range that includes the second m/z;
   (f) generating one or more second-generation product ion species from the isolated first subset of ion species by causing the isolated subset of the first-generation product ion species to be reacted with additional anions of the reagent compound for a second predetermined time duration during which either the first or a second supplemental oscillatory voltage waveform is applied to electrodes of the ion trap;
   (g) generating a plurality of fragment ion species by fragmenting the one or more second-generation product ion species;
   (i) generating a mass spectrum, using a mass analyzer of the mass spectrometer, of the fragment ion species; and
   (g) identifying the presence of the analyte compound within the sample based on a determined presence or absence of one or more predetermined fragment m/z values in the mass spectrum.

2. A method as recited in claim 1 wherein, during the generation of the plurality of second-generation product ion species, a second supplemental oscillatory voltage waveform is applied to electrodes of the ion trap, said second supplemental oscillatory voltage waveform comprising a wider range of frequencies than the first supplemental oscillatory voltage waveform.

3. A method as recited in claim 1 wherein, during the generation of the plurality of fragment ion species, a collision energy is chosen such that only a portion of ions of the protein or polypeptide ion species are fragmented.

4. A method as recited in claim 1, further comprising identifying the presence of a microorganism within a specimen from which the liquid sample was obtained, based on an identified presence of the protein or polypeptide in the liquid sample.

5. A method for identifying one or more protein or polypeptide compounds within a liquid sample comprising a mixture of compounds that includes a plurality of protein compounds or a plurality of polypeptide compounds or pluralities of both protein and polypeptide compounds, the method comprising:
   (a) forming positively charged ions of the mixture of compounds of the portion of the liquid sample by electrospray ionization in an ion source of a mass spectrometer, the positively charged ions comprising a plurality of ion species;
   (b) generating a mass spectrum of the ions using a mass analyzer of the mass spectrometer;
   (c) choosing a plurality of mass-to-charge ratio (m/z) ranges based on observable features in the mass spectrum; and
   (d) for each one of the chosen m/z ranges:
      (i) determining a charge state, $z_p$, corresponding to a mass spectral line observed at mass-to-charge ratio $(m/z)_p$ in the respective chosen m/z range and calculating mass value, $m_p$, as $m_p=(m/z)_p \times z_p$ and molecular weight, $MW=[z_p \times (m/z)_p] - z_p \times M_{proton}$, where $M_{proton}$ is the mass of a proton in AU;
      (ii) isolating a subset of the ion species having m/z values within the respective chosen m/z range;
      (iii) generating a plurality of first-generation product ion species from the respective isolated first subset of ion species by causing said respective isolated first subset of ion species to be reacted, in an ion trap, with anions of a reagent compound that, upon reaction, extract protons from each of one or more ion species that comprises a protonated molecular species of a protein or polypeptide compound, the reacting performed for a predetermined time duration during which a first supplemental oscillatory voltage waveform is applied to electrodes of the ion trap at a frequency that matches a frequency of motion of ions having a product-ion mass-to-charge ratio, $(m/z)_2$, given by $(m/z)_2 = (m_p - nM_{proton})/(z_p - n)$, where n is an integer such that $1 \leq n < z_p$ and $M_{proton}$ is the mass of a proton in AU;
      (iv) isolating a subset of the respective first-generation product ion species comprising another m/z range that includes the product-ion mass-to-charge ratio, $(m/z)_2$;
      (v) generating one or more second-generation product ion species from the respective isolated first subset of ion species by causing the isolated subset of the first-generation product ion species to be reacted with additional anions of the reagent compound for a second predetermined time duration during which either the first or a second supplemental oscillatory voltage waveform is applied to electrodes of the ion trap;
      (vi) generating a plurality of fragment ion species by fragmenting the one or more second-generation product ion species;
      (vii) generating a mass spectrum of the respective fragment ions; and
      (viii) searching for a protein or polypeptide identification based on the respective molecular weight and mass-to-charge values observed in the mass spectrum of the respective fragments.

6. A method as recited in claim 5 wherein, during the generation of the plurality of second-generation product ion species during at least one execution of step (v), a second supplemental oscillatory voltage waveform is applied to electrodes of the ion trap, said second supplemental oscillatory voltage waveform comprising a wider range of frequencies than that of the first supplemental oscillatory voltage waveform applied in the immediately preceding execution of step (iii).

7. A method as recited in claim 5 wherein, during the generation of the plurality of fragment ion species during at least one execution of step (vi), a collision energy is chosen such that only a portion of ions of the one or more second-generation product ion species are fragmented.

8. A method as recited in claim 5, further comprising identifying the presence of a microorganism within a specimen from which the liquid sample was obtained, based on an identified presence of one or more protein or polypeptide compounds in the liquid sample.

9. A method for identifying one or more protein or polypeptide compounds within a liquid sample comprising a mixture of compounds that includes a plurality of protein compounds or a plurality of polypeptide compounds or pluralities of both protein and polypeptide compounds, the method comprising:
   (a) forming positively charged ions of the mixture of compounds of the portion of the liquid sample by electrospray ionization in an ion source of a mass spectrometer, the positively charged ions comprising a plurality of ion species;
   (b) generating a mass spectrum of the ions, within a survey scan mass-to-charge ratio range, $\Delta(m/z)_{survey}$, using a mass analyzer of the mass spectrometer;
   (c) dividing the range, $\Delta(m/z)_{survey}$, into a plurality of mass-to-charge ratio (m/z) sub-ranges and
   (d) for each one of the m/z sub-ranges:
      (i) isolating a subset of the ion species having m/z values within the respective m/z sub-range;
      (ii) generating first-generation product ion species from the respective isolated first subset of ion species by causing said respective isolated first subset of ion species to be reacted, in an ion trap, with anions of a reagent compound that, upon reaction, extract protons from each of one or more ion species that comprises a protonated molecular species of a protein or polypeptide compound, the reacting performed for a predetermined time duration during which a supplemental oscillatory voltage waveform is applied to electrodes of the ion trap at a frequency that matches a frequency of motion of ions having a product-ion mass-to-charge ratio, $(m/z)_2$, that is greater than all m/z values encompassed within the respective sub-range;
      (iii) generating a plurality of fragment ion species by fragmenting the first-generation product ion species;
      (iv) generating a mass spectrum of the respective fragment ions; and
      (v) searching for a protein or polypeptide identification based on the value $(m/z)_2$ and mass-to-charge values observed in the mass spectrum of the respective fragments.

10. A method as recited in claim 9 wherein, during the generation of the plurality of fragment ion species during at least one execution of step (iii), a collision energy is chosen such that only a portion of ions of the first-generation product ion species are fragmented.

11. A method as recited in claim 9, further comprising identifying the presence of a microorganism within a specimen from which the liquid sample was obtained, based on an identified presence of the one or more protein or polypeptide compounds in the liquid sample.

12. A method for identifying one or more protein or polypeptide compounds within a liquid sample comprising a mixture of compounds that includes a plurality of protein compounds or a plurality of polypeptide compounds or pluralities of both protein and polypeptide compounds, the method comprising:
   (a) forming positively charged ions of the mixture of compounds of the portion of the liquid sample by electrospray ionization in an ion source of a mass spectrometer, the positively charged ions comprising a plurality of ion species;
   (b) generating a mass spectrum of the ions, within a survey scan mass-to-charge ratio range, $\Delta(m/z)_{survey}$, using a mass analyzer of the mass spectrometer;
   (c) dividing the range, $\Delta(m/z)_{survey}$, into a plurality of mass-to-charge ratio (m/z) sub-ranges and
   (d) for each one of the m/z sub-ranges:
      (i) isolating a subset of the ion species having m/z values within the respective m/z sub-range;
      (ii) generating a plurality of first-generation product ion species from the respective isolated first subset of ion species by causing said respective isolated first subset of ion species to be reacted, in an ion trap, with anions of a reagent compound that, upon reaction, extract protons from each of one or more ion species that comprises a protonated molecular species of a protein or polypeptide compound, the reacting performed for a predetermined time duration during which a plurality of n supplemental oscillatory voltage waveforms are applied to electrodes of the ion trap, each waveform having a respective frequency, $F_j$, $(1 \leq j \leq n)$ that matches a respective frequency of motion of ions having a product-ion mass-to-charge ratio, $(m/z)_j$, $(1 \leq j \leq n)$ that is greater than all m/z values encompassed within the respective sub-range;
      (iii) generating a plurality of fragment ion species by fragmenting the respective plurality of first-generation product ion species;
      (iv) generating a mass spectrum of the respective fragment ions; and
      (v) searching for a protein or polypeptide identification based on the values $(m/z)_j$ and mass-to-charge values observed in the mass spectrum of the respective fragments.

13. A method as recited in claim 12 wherein, during the generation of the plurality of fragment ion species during at least one execution of step (iii), a collision energy is chosen such that only a portion of ions of the first-generation product ion species are fragmented.

14. A method as recited in claim 12, further comprising identifying the presence of a microorganism within a specimen from which the liquid sample was obtained, based on an identified presence of the one or more protein or polypeptide compounds in the liquid sample.

* * * * *